United States Patent
Kimchi

(12) 
(10) Patent No.: US 7,026,148 B1
(45) Date of Patent: Apr. 11, 2006

(54) DAP-KINASE RELATED PROTEIN

(75) Inventor: Adi Kimchi, Raanana (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/719,748

(22) PCT Filed: Jun. 15, 1999

(86) PCT No.: PCT/US99/13411

§ 371 (c)(1),
(2), (4) Date: Feb. 27, 2001

(87) PCT Pub. No.: WO99/66030

PCT Pub. Date: Dec. 23, 1999

Related U.S. Application Data

(60) Provisional application No. 60/089,294, filed on Jun. 15, 1998.

(51) Int. Cl.
*C12N 9/12* (2006.01)
*C12N 15/00* (2006.01)
*C12N 1/20* (2006.01)
*C07K 1/00* (2006.01)
*C07H 21/04* (2006.01)

(52) U.S. Cl. .......................... 435/194; 435/6; 435/435; 435/252.3; 435/69.1; 530/350; 536/23.1; 536/23.2

(58) Field of Classification Search ................ 435/194, 435/6, 252.3, 320.1, 325, 69.1; 530/350; 536/23.2, 23.1
See application file for complete search history.

(56) References Cited

U.S. PATENT DOCUMENTS 5,958,748 A * 9/1999 Akira et al. ................ 435/194

FOREIGN PATENT DOCUMENTS

EP 911408 * 4/1999
WO WO 95/10630 4/1995

OTHER PUBLICATIONS

Inbal et al., SPTREMBL Database, Accession No. O75892, Nov. 1998.*
Kawai et al., Mol. Cell. Biol., 18, 1642-1651, Mar. 1998.*
Deiss et al., Genes Dev., 9, 15-30, 1995.*
Marra et al., EST Database, Accession No. W82116, Sep. 1996.*
Deiss et al., "Identification of a novel serine/threonine kinase and a novel 15-kD protein as potential mediators of the Y interferon-induced cell death", *Genes & Development*, 9:15-30 (1995).
Database EST, Accession No. H27327, Jul. 1995.
Cohen, O., Feinstein, E., and Kimchi, A., "DAP-kinase is a Ca2+/calmodulin-dependent, cytoskeletal-associated protein kinase, with cell death-inducing functions that depend on its catalytic activity", *EMEBO, J.*, 16, 998-1008, 1997.
Cohen, O., Inbal, B., Kissil, U., Feinstein, E., Spivak, T., and Kimchi, A., "DAP-kinase participates in TNF-a and Fas-induced apoptosis and its function requires the death domain.", 1. *Cell. Biol.* vol. 246, No. 1, 141-148, 1999.
Deiss, L.P., Feinstein, E., Berissi, H., Cohen, O., and Kimchi A., "Identification of a novel serine/threonine kinase and a novel 15-kD protein as potential mediators of the gamma interferon-induced cell death.", *Genes Dev.,* 9; 15-30, 1995.
Deiss, L.P. and Kimchi A., "A genetic tool used to identify thioredaxin as a mediator of a growth inhibitory signal.", *Science*, 252, 117-120, 1991.
del Peso, L., Gonzalez-Garcia, M., Page, C., Herrera, R., and Nunez, G., "Interleukin-3- phosphorylation of BAD through the protein kinase Akt.", *Science* 282, 318-321, 19-97.
Green, D., and Kroemer, G., "The central executioners of apoptosis: caspases or mitochondria?" *Trends Cell Biol.*, 8, 267-271, 1998.
Gross, G. et al., *Proc. Natl. Acad. Sci. USA* 86, 10024-82, 1989.

(Continued)

*Primary Examiner*—Maryam Monshipouri
(74) *Attorney, Agent, or Firm*—Browdy and Neimark

(57) ABSTRACT

A new protein, which is a novel homologue of DAP-kinase, has been isolated. This novel calmodulin-dependent kinase is a cell death-promoting protein functioning in the biochemical pathway which involves DAP (death-associated protein)—kinase (e.g., forming a cascade of sequential kinases, one directly activating the other). Alternatively, the two kinases may operate to promote cell death in parallel pathways.

30 Claims, 16 Drawing Sheets

OTHER PUBLICATIONS

Hanks, S.K., and Quinn, A.M., "Protein kinase catalytic domain sequence database: identification of conserved features of primary structure and classification of family members.", *Methods Enzymol.*, 200,38-62, 1991.

Inbal, B., Cohen, O., Polak-Charcon, S., Kopolovic, J., Vadai, E., Eisenbach, L., and Kimchi, A., "DAP kinase links the control of apoptosis to metastasis.", *Nature*, 390, 180-1-04, 1997.

Jacobson, M.D., Weil, M., and Raff, M.C., Programmed cell death in a animal development. *Cell*, 88, 347-3, 54, 1997.

Kawai, T., Matsumoto, M., Takeda, K., Sanjo, H., and Akira, S., "ZIP kinase, a novel serine/threonine kinase which mediates apoptosis.", *Mol. Cell Biol.* 18, 1642-1651, 1998.

Kelliher, M.A., Grimm, S., Ishida, Y., Kuo, F., Stanger, B.Z., and Leder, P., "The death domain kinase RIP mediates the TNF-induced NF-kappaB signal.", *Immunity*, 8, 297-303, 1998.

Kimchi, A., *J. Cell. Biochem.*, 50, 1-9, 1992.

Kimchi, A., "DAP genes: novel apoptotic genes isolated by a functional approach to gene cloning.", *Biochim. Biophys. Act*, 1377, F13-33, 1998.

Kissil, J.L., and Kimchi, A., "Death-associated proteins: from gene identification to a the analysis of their apoptotic and tumor suppressive functions.", *Mol. Med. Today*, 4, 268-74, 1998.

Kissil, I.L., Cohen, O., Raveh, T., and Kimchi, A., "Structure-function analysis of an evolutionary conserved protein DAP3, which mediates TNF-α- and Fas-induced cell death", *EMBO J.*, 18, 3 53 -362, 1999.

Kogel, D., Plottner, O., Landsberg, G., Christian, S., and Scheidtmann, K.H., Cloning and characterization of Dlk, a novel serine/threonine kinase that is tightly associated with chromatin and phosphorylates core histones., *Oncogene*, 17, 2645-2654, 1998.

Levy et al., *Mol. Cell. Biol*, 13, 7942-7952, 1993.

Levy-Strumpf, N., and Kimchi, A., "Death associated proteins (DAPs): from gene identification to the analysis of their apoptotic and tumor suppressive functions." *Oncogene*, 17,3331-3340, 1998.

Maundrell, K., Antonsson, B., Magnenat, E., Camps, M., Muda, M., Chabert, C., Gillieron, C., Boschert, U., Vial-Knecht, E., Martinou, J.C., and Artkinstall, S., "Bcl-2 undergoes phosphorylation by c-Jun N-terminal kinase/stress-activated protein kinases in the presence of the constitutively active GTP-binding protein Racl.", *J. Biol. Chem.*, 272, 25238-25342, 1997.

McCarthy, IV., Mi, I , and Dixit, V.M., "RIP2 is a novel NF-kappaB-activating and cell death-inducing kinase," *J. Biol. Chem.*, 273, 16968-75, 1998.

Park, J., Kim, I., Oh, Y.J., Lee, K., Han, P.L., and Choi, E.J., "Activation of c-Jun N-terminal kinase antagonizes an anti-apoptotic action of Bcl-2.", *J. Biol. Chem.*, 272, 16725-16728, 1997.

Sanjo, H., Kawai, T., and Akira, S., "DRAKS, a novel serine/threonine kinases related to death-associated protein kinase that trigger apoptosis.", *J. Biol, Chem.*, 273, 29066-29071, 1998.

Stanger, B.Z., Leder, P., Lee, T.H., Kim, E., and Seed, B., "RIP: a novel protein containing a death domain that interacts with Fas/APO-1 (CD95) in yeast and causes cell death.", *Cell* 81, 513-523) 1995.

Sun, X, Lee, J., Navas, T., Baldwin, D.T., Stewart, T.A., and Dixit, V.M., "RIP3, a Novel Apoptosis-inducing Kinase.", *J. Biol. Chem.*, 274, 16871-16875, 1999.

White, E., "Life, death and the pursuit of apoptosis.", *Genes Dev.*, 10, 1- 15, 1996.

Yang, X., Khosravi-Far, R., Chang, H.Y., and Baltimore, D., *Cell* 89, 1067-1067, 1997.

* cited by examiner

FIG. 1

```
GACCGCGGCAGCTCAGCCTCCCGCCGATTGTATGTTCCAGGCCTCAATGAGGAGTCCAAA    60
        M  E  P  F  K  Q  Q  K  V  E  D  F  Y  D  I  G  E  E  L  G     20
C ATG GAGCCATTCAAGCAGCAGAAGGTGGAGGACTTTTATGACATCGGAGAGGAGCTGGG   120
  S  G  Q  F  A  I  V  K  K  C  R  E  K  S  T  G  L  E  Y  A     40
GAGTGGCCAGTTTGCCATCGTGAAGAAGTGCCGGGAGAAGAGCACGGGGCTTGAGTATGC   180
  A  K  F  I  K  K  R  Q  S  R  A  S  R  R  G  V  S  R  E  E     60
AGCCAAGTTCATCAAGAAGCGGCAGAGCCGGGCGAGCCGGCGCGGTGTGAGCCGGGAGGA   240
  I  E  R  E  V  S  I  L  R  Q  V  L  H  H  N  V  I  T  H      80
GATCGAGCGGGAGGTGAGCATCCTGCGGCAGGTGCTGCACCACAATGTCATCACGCTGCA   300
  D  V  Y  E  N  R  T  D  V  V  L  I  L  E  L  V  S  G  G  E   100
CGACGTCTATGAGAACCGCACCGACGTGGTGCTCATCCTTGAGCTAGTGTCTGGAGGAGA   360
  L  F  D  F  L  A  Q  K  E  S  L  S  E  E  E  A  T  S  F  I   120
GCTCTTCGATTTCCTGGCCCAGAAGGAGTCACTGAGTGAGGAGGAGGCCACCAGCTTCAT   420
  K  Q  I  L  D  G  V  N  Y  L  H  T  K  K  I  A  H  F  D  L   140
TAAGCAGATCCTGGATGGGGTGAACTACCTTCACACAAAGAAAATTGCTCACTTTGATCT   480
  K  P  E  N  I  M  L  L  D  K  N  I  P  I  P  H  I  K  L  I   160
CAAGCCAGAAAACATTATGTTGTTAGACAAGAATATTCCCATTCCACACATCAAGCTGAT   540
  D  F  G  L  A  H  E  I  E  D  G  V  E  F  K  N  I  F  G  T   180
TGACTTTGGTCTGGCTCACGAAATAGAAGATGGAGTTGAATTTAAGAATATTTTTGGGAC   600
  P  E  F  V  A  P  E  I  V  N  Y  E  P  L  G  L  E  A  D  M   200
GCCGGAATTTGTTGCTCCAGAAATTGTGAACTACGAGCCCCTGGGTCTGGAGGCTGACAT   660
  W  S  I  G  V  I  T  Y  I  L  L  S  G  A  S  P  F  L  G  D   220
GTGGAGCATAGGCGTCATCACCTACATCCTCTTAAGTGGAGCATCCCCTTTCCTGGGAGA   720
  T  K  Q  E  T  L  A  N  I  T  S  V  S  Y  D  F  D  E  E  F   240
CACGAAGCAGGAAACACTGGCAAATATCACATCAGTGAGTTACGACTTTGATGAGGAATT   780
  F  S  H  T  S  E  L  A  K  D  F  I  R  K  L  L  V  K  E  T   260
CTTCAGCCATACGAGCGAGCTGGCCAAGGACTTTATTCGGAAGCTTCTGGTTAAAGAGAC   840
  R  K  R  L  T  I  Q  E  A  L  R  H  P  W  I  T  P  V  D  N   280
CCGGAAACGGCTCACAATCCAAGAGGCTCTCAGACACCCCTGGATCACGCCGGTGGACAA   900
  Q  Q  A  M  V  R  R  E  S  V  V  N  L  E  N  F  R  K  Q  Y   300
CCAGCAAGCCATGGTGCGCAGGGAGTCTGTGGTCAATCTGGAGAACTTCAGGAAGCAGTA   960
  V  R  R  R  W  K  L  S  F  S  I  V  S  L  C  N  H  L  T  R   320
TGTCCGCAGGCGGTGGAAGCTTTCCTTCAGCATCGTGTCCCTGTGCAACCACCTCACCCG  1020
  S  L  M  K  K  V  H  L  R  P  D  E  D  L  R  N  C  E  S  D   340
CTCGCTGATGAAGAAGGTGCACCTGAGGCCGGATGAGGACCTGAGGAACTGTGAGAGTGA  1080
  T  E  E  D  I  A  R  R  K  A  L  H  P  R  R  R  S  S  T  S   360
CACTGAGGAGGACATCGCCAGGAGGAAAGCCCTCCACCCACGGAGGAGGAGCAGCACCTC  1140
C TAA CTGGCCTGACCTGCAGTGGCCGCCAGGGAGGTTTGGGCCCAGCGGGGCTCCCTTCT  1200
GTGCAGACTTTTGGACCCAGCTCAGCACCAGCACCCGGGCGTCCTGAGCACTTTGCAAGA  1260
GAGATGGGCCCAAGGAATTCAGAAGAGCTTGCAGGCAAGCCAGGAGACCCTGGGAGCTGT  1320
GGCTGTCTTCTGTGGAGGAGGCTCCAGCATTCCCAAAGCTCTTAATTCTCCATAAAATGG  1380
GCTTTCCTCTGTCTGCCATCCTCAGAGTCTGGGGTGGAGTGTGGACTTAGGAAAACAAT  1440
ATAAAGGACATCCTCATCATCACGGGGTGAAGGTCAGAGTAAGGCAGCCTTCTTCACAGG  1500
CTGAGGGGGTTCAGAACCAGCCTGGCCAAAAATTACACCAGAGAGACAGAGTCCTCCCCA  1560
TTGGGAACAGGGTGATTGAGGAAAGTGAACCTTgGGTGTGAGGGACCAATCCTGTGACCT  1620
CCCAGAACCATGGAAGCCAGGACGTCAGGCTGaCCAACACCTCAGACCTTCTGAAGCAGC  1680
CCATTGcTGGCCCGCCATGTTGTAATTTTGCTCATTTTTATTAAActtctggtttacctg  1740
aa                                                            1742
```

FIG. 2A

```
DAP-kinase   13  YDTGEELGSGQFAVVKCREKSTGLQYAAKFIK
ZIP-kinase   13  YEMGEELGSGQFAIVRKCRQKGTGKEYAAKFIK
DRP-1        13  YDIGEELGSGQFAIVKKCREKSTGLEYAAKFIK
DRAK1        61  LCPGRELGRGKFAVVRKCIKKDSGKEFAAKFMR
DRAK2        33  ILTSKELGRGKFAVVRQCISKSTGQEYAAKFLR DAP-kinase   46  KRRTKSSRRGVSREDIEREVSILKEI-QHPNVI
ZIP-kinase   46  KRRLSSSRRGVSREEIEREVNILREI-RHPNII
DRP-1        46  KRQSRASRRGVSREEIEREVSILRQV-LHHNVI
DRAK1        94  KRR----KGQDCRMEIIHEIAVLELAQDMPWVI
DRAK2        66  KRR----RGQDCRAEILHEIAVLELAKSCPRVI DAP-kinase   78  TLHEVYENKTDVILILELVAGGELFD-FLAEK-
ZIP-kinase   78  TLHDIFENKTDVVLILELVSGGELFD-FLAEK-
DRP-1        78  TLHDVYENRTDVVLILELVSGGELFD-FLAQK-
DRAK1       123  NLHEVYETASEMILVLEYAAGGEIFDQCVADRE
DRAK2        95  NLHEVYENTSEIILILEYAAGGEIFSLCLPELA DAP-kinase  109  ESLTEEEATEFLKQILNGVYYLHSLQIAHFDLK
ZIP-kinase  109  ESLTEDEATQFLKQILDGVHYLHSKRIAHFDLK
DRP-1       109  ESLSEEEATSFIKQILDGVNYLHTKKIAHFDLK
DRAK1       156  EAFKEKDVQRLMRQILEGVHFLHTRDVVHLDLK
DRAK2       128  EMVSENDVIRLIKQILEGVYYLEQNNIVHLDLK DAP-kinase  142  PENIMLLDRNVPKPRIKIIDFGLAHKIDFGNEF
ZIP-kinase  142  PENIMLLDKNVPNPRIKLIDFGIAHKIEAGNEF
DRP-1       142  PENIMLLDKNIPIPHIKLIDFGLAHEIEDGVEF
DRAK1       189  PQNILLTSESPLGD-IKIVDFGLSRILKNSEEL
DRAK2       161  PQNILLSSIYPLGD-IKIVDFGMSRKIGHACEL DAP-kinase  175  KNIFGTPEFVAPEIVNYEPLGLEADMWSIGVIT
ZIP-kinase  175  KNIFGTPEFVAPEIVNYEPLGLEADMWSIGVIT
DRP-1       175  KNIFGTPEFVAPEIVNYEPLGLEADMWSIGVIT
DRAK1       221  REIMGTPEYVAPEILSYDPISMATDMWSIGVLT
DRAK2       193  REIMGTPEYLAPEILNYDPITTATDMWNIGITA DAP-kinase  208  YILLSGASPFLGDTKQETLANVSAVNYEFEDEY
ZIP-kinase  208  YILLSGASPFLGETKQETLTNISAVNYDFDEEY
DRP-1       208  YILLSGASPFLGDTKQETLANITSVSYDFDEEF
DRAK1       254  YVMLTGISPFLGNDKQETFLNISQMNLSYSEEE
DRAK2       226  YMLLTHTSPFVGEDNQETYLNISQVNVDYSEET DAP-kinase  241  FSNTSALAKDFIRRLLVKDPKKRMTIQDSLQHP
ZIP-kinase  241  FSNTSELAKDFIRRLLVKDPKRRMTIAQSLEHS
DRP-1       241  FSHTSELAKDFIRKLLVKETRKRLTIQEALRHP
DRAK1       287  FDVLSESAVDFIRTLLVKKPEDRATAEECLKHP
DRAK2       259  FSSVSQLATDFIQSLLVKNPEKRPTAEICLSHS DAP-kinase  274  WI
ZIP-kinase  274  WI
DRP-1       274  WI
DRAK1       320  WL
DRAK2       292  WL
```

FIG. 2B

```
DAP-kinase  1  NMEKFKK---FAARKKWKQSVRLISLCQRLSR   29
DRP-1       1  NLENFRK---QYVRRRWKLSFSIVSLCNHLTR   29
smMLCK      1  SKDRMKK---YMARRKWQKTGHAVRAIGRLSS   29
CaMKIIa     1  TVDCLKK---LNARRKLKGAILTTMLATRNFS   29
CaMKI       1  VSEQIKK---NFAKSKWKQAFNAT-AVVRHMR   28
CaMKIV      1  MDTAQKKLQEFNARRKLKAAVKAVVASSRLGS   32

ZIP-kinase  1  GEDSGRK----PERRRLKTTRLKEYTIKSHSS   28
```

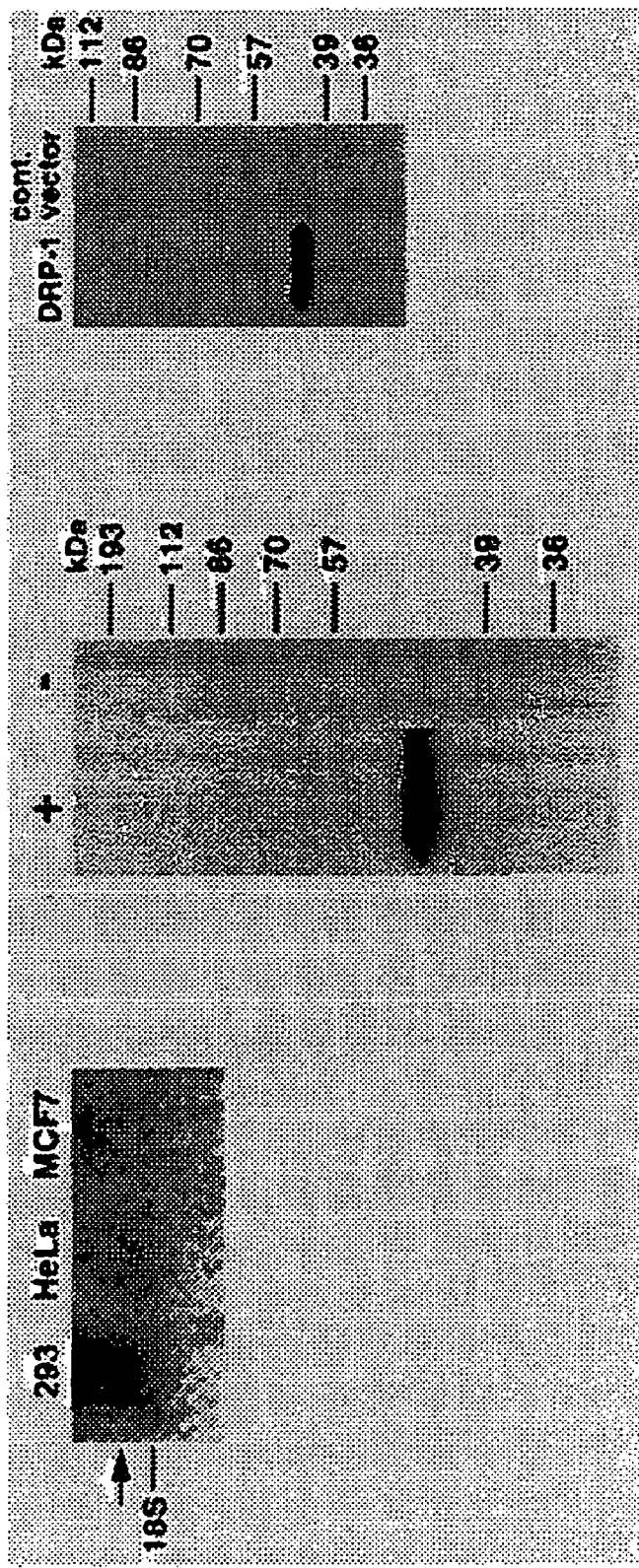

MOCK

DRP-1

Anti-Flag

Anti-Vinculin

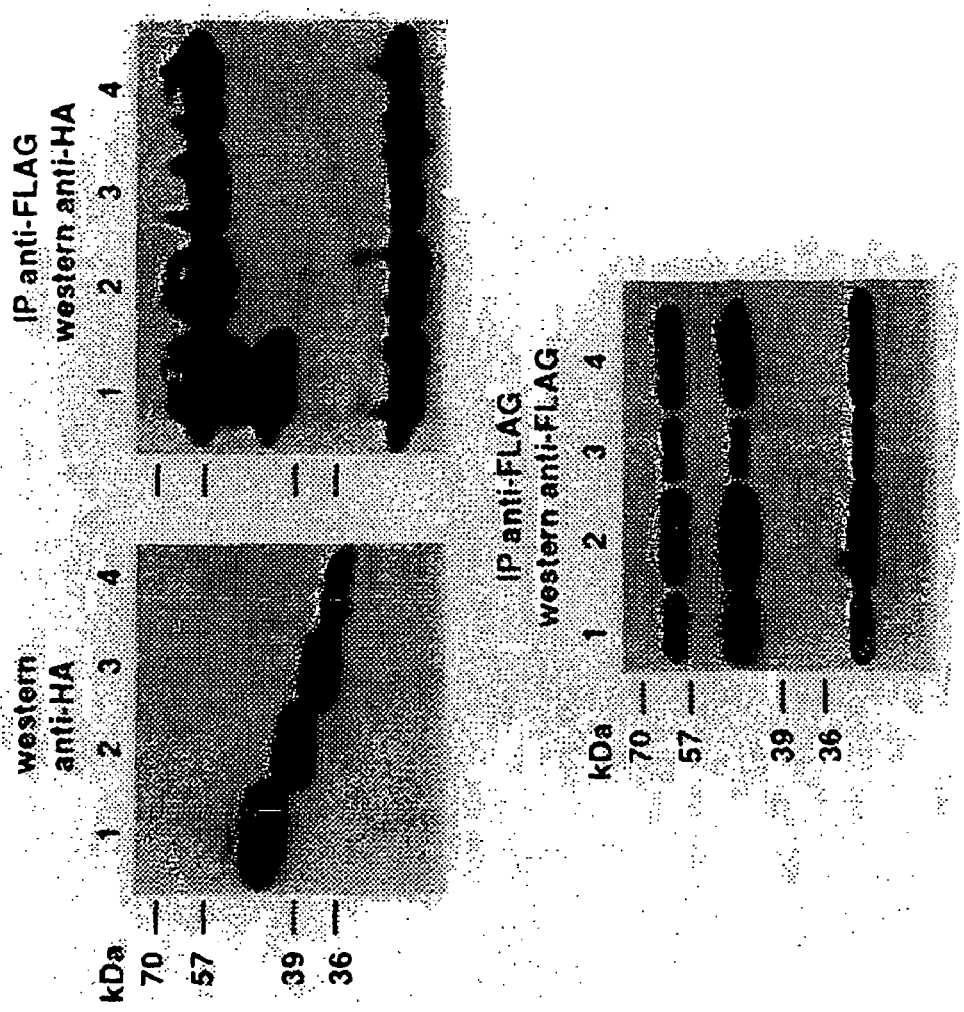

SEQUENCE LISTING

<160> NUMBER OF SEQ ID NOS: 14

<210> SEQ ID NO 1
<211> LENGTH: 1742
<212> TYPE: DNA
<213> ORGANISM: Human
<220> FEATURE:
<221> NAME/KEY: CDS
<222> LOCATION: (62)..(1141)

<400> SEQUENCE: 1

```
gaccgcggca gctcagcctc ccgccgattg tatgttccag gcctcaatga ggagtccaaa        60 c atg gag cca ttc aag cag cag aag gtg gag gac ttt tat gac atc gga      109
  Met Glu Pro Phe Lys Gln Gln Lys Val Glu Asp Phe Tyr Asp Ile Gly
  1               5                  10                  15 gag gag ctg ggg agt ggc cag ttt gcc atc gtg aag aag tgc cgg gag        157
Glu Glu Leu Gly Ser Gly Gln Phe Ala Ile Val Lys Lys Cys Arg Glu
             20                  25                  30 aag agc acg ggg ctt gag tat gca gcc aag ttc atc aag aag cgg cag        205
Lys Ser Thr Gly Leu Glu Tyr Ala Ala Lys Phe Ile Lys Lys Arg Gln
         35                  40                  45 agc cgg gcg agc cgg cgc ggt gtg agc cgg gag gag atc gag cgg gag        253
Ser Arg Ala Ser Arg Arg Gly Val Ser Arg Glu Glu Ile Glu Arg Glu
     50                  55                  60 gtg agc atc ctg cgg cag gtg ctg cac cac aat gtc atc acg ctg cac        301
Val Ser Ile Leu Arg Gln Val Leu His His Asn Val Ile Thr Leu His
65                  70                  75                  80 gac gtc tat gag aac cgc acc gac gtg gtg cac atc ctt gag cta gtg        349
Asp Val Tyr Glu Asn Arg Thr Asp Val Val His Ile Leu Glu Leu Val
                 85                  90                  95 tct gga gga gag ctc ttc gat ttc ctg gcc cag aag gag tca ctg agt        397
Ser Gly Gly Glu Leu Phe Asp Phe Leu Ala Gln Lys Glu Ser Leu Ser
            100                 105                 110 gag gag gag gcc acc agc ttc att aag cag atc ctg gat ggg gtg aac        445
Glu Glu Glu Ala Thr Ser Phe Ile Lys Gln Ile Leu Asp Gly Val Asn
        115                 120                 125 tac ctt cac aca aag aaa att gct cac ttt gat ctc aag cca gaa aac        493
Tyr Leu His Thr Lys Lys Ile Ala His Phe Asp Leu Lys Pro Glu Asn
    130                 135                 140 att atg ttg tta gac aag aat att ccc att cca cac atc aag ctg att        541
Ile Met Leu Leu Asp Lys Asn Ile Pro Ile Pro His Ile Lys Leu Ile
145                 150                 155                 160 gac ttt ggt ctg gct cac gaa ata gaa gat gga gtt gaa ttt aag aat        589
Asp Phe Gly Leu Ala His Glu Ile Glu Asp Gly Val Glu Phe Lys Asn
                165                 170                 175 att ttt ggg acg ccg gaa ttt gtt gct cca gaa att gtg aac tac gag        637
Ile Phe Gly Thr Pro Glu Phe Val Ala Pro Glu Ile Val Asn Tyr Glu
            180                 185                 190 ccc ctg ggt ctg gag gct gac atg tgg agc ata ggc gtc atc acc tac        685
Pro Leu Gly Leu Glu Ala Asp Met Trp Ser Ile Gly Val Ile Thr Tyr
        195                 200                 205 atc ctc tta agt gga gca tcc cct ttc ctg gga gac acg aag cag gaa        733
Ile Leu Leu Ser Gly Ala Ser Pro Phe Leu Gly Asp Thr Lys Gln Glu
    210                 215                 220 aca ctg gca aat atc aca tca gtg agt tac gac ttt gat gag gaa ttc        781
Thr Leu Ala Asn Ile Thr Ser Val Ser Tyr Asp Phe Asp Glu Glu Phe
225                 230                 235                 240 ttc agc cat acg agc gag ctg gcc aag gac ttt att cgg aag ctt ctg        829
Phe Ser His Thr Ser Glu Leu Ala Lys Asp Phe Ile Arg Lys Leu Leu
```

```
                             245                 250                 255
gtt aaa gag acc cgg aaa cgg ctc aca atc caa gag gct ctc aga cac         877
Val Lys Glu Thr Arg Lys Arg Leu Thr Ile Gln Glu Ala Leu Arg His
            260                 265                 270 ccc tgg atc acg ccg gtg gac aac cag caa gcc atg gtg cga cgg gag         925
Pro Trp Ile Thr Pro Val Asp Asn Gln Gln Ala Met Val Arg Arg Glu
        275                 280                 285 tct gtg gtc aat ctg gag aac ttc agg aag cag tat gtc cgc agg cgg         973
Ser Val Val Asn Leu Glu Asn Phe Arg Lys Gln Tyr Val Arg Arg Arg
    290                 295                 300 tgg aag ctt tcc ttc agc atc gtg tcc ctg tgc aac cac ctc acc cgc        1021
Trp Lys Leu Ser Phe Ser Ile Val Ser Leu Cys Asn His Leu Thr Arg
305                 310                 315                 320 tcg ctg atg aag aag gtg cac ctg agg ccg gat gag gac ctg agg aac        1069
Ser Leu Met Lys Lys Val His Leu Arg Pro Asp Glu Asp Leu Arg Asn
                325                 330                 335 tgt gag agt gac act gag gag gac atc gcc agg agg aaa gcc ctc cac        1117
Cys Glu Ser Asp Thr Glu Glu Asp Ile Ala Arg Arg Lys Ala Leu His
            340                 345                 350 cca cgg agg agg agc agc acc tcc taactggcct gacctgcagt ggccgccagg       1171
Pro Arg Arg Arg Ser Ser Thr Ser
        355                 360 gaggtttggg cccagcgggg ctcccttctg tgcagacttt tggacccagc tcagcaccag      1231 caccccgggcg tcctgagcac tttgcaagag agatgggccc aaggaattca gaagagcttg    1291
caggcaagcc aggagaccct gggagctgtg gctgtcttct gtggaggagg ctccagcatt     1351
cccaaagctc ttaattctcc ataaaatggg ctttcctctg tctgccatcc tcagagtctg     1411
gggtgggagt gtggacttag gaaaacaata taaaggacat cctcatcatc acggggtgaa     1471
ggtcagagta aggcagcctt cttcacaggc tgaggggtt cagaaccagc ctggccaaaa      1531
attacaccag agagacagag tcctccccat tgggaacagg gtgattgagg aaagtgaacc     1591
ttgggtgtga gggaccaatc ctgtgacctc ccagaaccat ggaagccagg acgtcaggct     1651
gaccaacacc tcagaccttc tgaagcagcc cattgctggc ccgccatgtt gtaattttgc     1711
tcatttttat taaacttctg gtttacctga a                                    1742

<210> SEQ ID NO 2
<211> LENGTH: 360
<212> TYPE: PRT
<213> ORGANISM: Human

<400> SEQUENCE: 2

Met Glu Pro Phe Lys Gln Gln Lys Val Glu Asp Phe Tyr Asp Ile Gly
  1               5                  10                  15

Glu Glu Leu Gly Ser Gly Gln Phe Ala Ile Val Lys Lys Cys Arg Glu
             20                  25                  30

Lys Ser Thr Gly Leu Glu Tyr Ala Ala Lys Phe Ile Lys Lys Arg Gln
         35                  40                  45

Ser Arg Ala Ser Arg Arg Gly Val Ser Arg Glu Glu Ile Glu Arg Glu
     50                  55                  60

Val Ser Ile Leu Arg Gln Val Leu His His Asn Val Ile Thr Leu His
 65                  70                  75                  80

Asp Val Tyr Glu Asn Arg Thr Asp Val Val His Ile Leu Glu Leu Val
                 85                  90                  95

Ser Gly Gly Glu Leu Phe Asp Phe Leu Ala Gln Lys Glu Ser Leu Ser
            100                 105                 110
```

-continued

```
Glu Glu Glu Ala Thr Ser Phe Ile Lys Gln Ile Leu Asp Gly Val Asn
            115                 120                 125

Tyr Leu His Thr Lys Lys Ile Ala His Phe Asp Leu Lys Pro Glu Asn
        130                 135                 140

Ile Met Leu Leu Asp Lys Asn Ile Pro Ile Pro His Ile Lys Leu Ile
145                 150                 155                 160

Asp Phe Gly Leu Ala His Glu Ile Glu Asp Gly Val Glu Phe Lys Asn
                165                 170                 175

Ile Phe Gly Thr Pro Glu Phe Val Ala Pro Glu Ile Val Asn Tyr Glu
            180                 185                 190

Pro Leu Gly Leu Glu Ala Asp Met Trp Ser Ile Gly Val Ile Thr Tyr
        195                 200                 205

Ile Leu Leu Ser Gly Ala Ser Pro Phe Leu Gly Asp Thr Lys Gln Glu
210                 215                 220

Thr Leu Ala Asn Ile Thr Ser Val Ser Tyr Asp Phe Asp Glu Glu Phe
225                 230                 235                 240

Phe Ser His Thr Ser Glu Leu Ala Lys Asp Phe Ile Arg Lys Leu Leu
                245                 250                 255

Val Lys Glu Thr Arg Lys Arg Leu Thr Ile Gln Glu Ala Leu Arg His
            260                 265                 270

Pro Trp Ile Thr Pro Val Asp Asn Gln Gln Ala Met Val Arg Arg Glu
        275                 280                 285

Ser Val Val Asn Leu Glu Asn Phe Arg Lys Gln Tyr Val Arg Arg Arg
    290                 295                 300

Trp Lys Leu Ser Phe Ser Ile Val Ser Leu Cys Asn His Leu Thr Arg
305                 310                 315                 320

Ser Leu Met Lys Lys Val His Leu Arg Pro Asp Glu Asp Leu Arg Asn
                325                 330                 335

Cys Glu Ser Asp Thr Glu Glu Asp Ile Ala Arg Arg Lys Ala Leu His
            340                 345                 350

Pro Arg Arg Arg Ser Ser Thr Ser
        355                 360

<210> SEQ ID NO 3
<211> LENGTH: 263
<212> TYPE: PRT
<213> ORGANISM: Human

<400> SEQUENCE: 3

Tyr Asp Thr Gly Glu Glu Leu Gly Ser Gly Gln Phe Ala Val Val Lys
1               5                   10                  15

Lys Cys Arg Glu Lys Ser Thr Gly Leu Gln Tyr Ala Ala Lys Phe Ile
            20                  25                  30

Lys Lys Arg Arg Thr Lys Ser Ser Arg Arg Gly Val Ser Arg Glu Asp
        35                  40                  45

Ile Glu Arg Glu Val Ser Ile Leu Lys Glu Ile Gln His Pro Asn Val
    50                  55                  60

Ile Thr Leu His Glu Val Tyr Glu Asn Lys Thr Asp Val Ile Leu Ile
65                  70                  75                  80

Leu Glu Leu Val Ala Gly Gly Glu Leu Phe Asp Phe Leu Ala Glu Lys
                85                  90                  95

Glu Ser Leu Thr Glu Glu Glu Ala Thr Glu Phe Leu Lys Gln Ile Leu
            100                 105                 110

Asn Gly Val Tyr Tyr Leu His Ser Leu Gln Ile Ala His Phe Asp Leu
        115                 120                 125
```

```
Lys Pro Glu Asn Ile Met Leu Leu Asp Arg Asn Val Pro Lys Pro Arg
        130                 135                 140

Ile Lys Ile Ile Asp Phe Gly Leu Ala His Lys Ile Asp Phe Gly Asn
145                 150                 155                 160

Glu Phe Lys Asn Ile Phe Gly Thr Pro Glu Phe Val Ala Pro Glu Ile
                165                 170                 175

Val Asn Tyr Glu Pro Leu Gly Leu Glu Ala Asp Met Trp Ser Ile Gly
            180                 185                 190

Val Ile Thr Tyr Ile Leu Leu Ser Gly Ala Ser Pro Phe Leu Gly Asp
            195                 200                 205

Thr Lys Gln Glu Thr Leu Ala Asn Val Ser Ala Val Asn Tyr Glu Phe
        210                 215                 220

Glu Asp Glu Tyr Phe Ser Asn Thr Ser Ala Leu Ala Lys Asp Phe Ile
225                 230                 235                 240

Arg Arg Leu Leu Val Lys Asp Pro Lys Lys Arg Met Thr Ile Gln Asp
                245                 250                 255

Ser Leu Gln His Pro Trp Ile
        260

<210> SEQ ID NO 4
<211> LENGTH: 263
<212> TYPE: PRT
<213> ORGANISM: Human

<400> SEQUENCE: 4

Tyr Glu Met Gly Glu Glu Leu Gly Ser Gly Gln Phe Ala Ile Val Arg
  1               5                  10                  15

Lys Cys Arg Gln Lys Gly Thr Gly Lys Glu Tyr Ala Ala Lys Phe Ile
             20                  25                  30

Lys Lys Arg Arg Leu Ser Ser Ser Arg Arg Gly Val Ser Arg Glu Glu
         35                  40                  45

Ile Glu Arg Glu Val Asn Ile Leu Arg Glu Ile Arg His Pro Asn Ile
     50                  55                  60

Ile Thr Leu His Asp Ile Phe Glu Asn Lys Thr Asp Val Val Leu Ile
 65                  70                  75                  80

Leu Glu Leu Val Ser Gly Gly Glu Leu Phe Asp Phe Leu Ala Glu Lys
                 85                  90                  95

Glu Ser Leu Thr Glu Asp Glu Ala Thr Gln Phe Leu Lys Gln Ile Leu
            100                 105                 110

Asp Gly Val His Tyr Leu His Ser Lys Arg Ile Ala His Phe Asp Leu
        115                 120                 125

Lys Pro Glu Asn Ile Met Leu Leu Asp Lys Asn Val Pro Asn Pro Arg
    130                 135                 140

Ile Lys Leu Ile Asp Phe Gly Ile Ala His Lys Ile Glu Ala Gly Asn
145                 150                 155                 160

Glu Phe Lys Asn Ile Phe Gly Thr Pro Glu Phe Val Ala Pro Glu Ile
                165                 170                 175

Val Asn Tyr Glu Pro Leu Gly Leu Glu Ala Asp Met Trp Ser Ile Gly
            180                 185                 190

Val Ile Thr Tyr Ile Leu Leu Ser Gly Ala Ser Pro Phe Leu Gly Glu
            195                 200                 205

Thr Lys Gln Glu Thr Leu Thr Asn Ile Ser Ala Val Asn Tyr Asp Phe
        210                 215                 220

Asp Glu Glu Tyr Phe Ser Asn Thr Ser Glu Leu Ala Lys Asp Phe Ile
```

```
                225                 230                 235                 240
Arg Arg Leu Leu Val Lys Asp Pro Lys Arg Arg Met Thr Ile Ala Gln
                    245                 250                 255

Ser Leu Glu His Ser Trp Ile
                260

<210> SEQ ID NO 5
<211> LENGTH: 261
<212> TYPE: PRT
<213> ORGANISM: Human

<400> SEQUENCE: 5

Leu Cys Pro Gly Arg Glu Leu Arg Gly Lys Phe Ala Val Val Arg
  1               5                  10                  15

Lys Cys Ile Lys Lys Asp Ser Gly Glu Phe Ala Ala Lys Phe Met
                 20                  25                  30

Arg Lys Arg Arg Lys Gly Gln Asp Cys Arg Met Glu Ile Ile His Glu
             35                  40                  45

Ile Ala Val Leu Glu Leu Ala Gln Asp Asn Pro Trp Val Ile Asn Leu
         50                  55                  60

His Glu Val Tyr Glu Thr Ala Ser Glu Met Ile Leu Val Leu Glu Tyr
 65                  70                  75                  80

Ala Ala Gly Gly Glu Ile Phe Asp Gln Cys Val Ala Asp Arg Glu Glu
                 85                  90                  95

Ala Phe Lys Glu Lys Asp Val Gln Arg Leu Met Arg Gln Ile Leu Glu
                100                 105                 110

Gly Val His Phe Leu His Thr Arg Asp Val Val His Leu Asp Leu Lys
            115                 120                 125

Pro Gln Asn Ile Leu Leu Thr Ser Glu Ser Pro Leu Gly Asp Ile Lys
        130                 135                 140

Ile Val Asp Phe Gly Leu Ser Arg Ile Leu Lys Asn Ser Glu Glu Leu
145                 150                 155                 160

Arg Glu Ile Met Gly Thr Pro Glu Tyr Val Ala Pro Glu Ile Leu Ser
                165                 170                 175

Tyr Asp Pro Ile Ser Met Ala Thr Asp Met Trp Ser Ile Gly Val Leu
            180                 185                 190

Thr Tyr Val Met Leu Thr Gly Ile Ser Pro Phe Leu Gly Asn Asp Lys
        195                 200                 205

Gln Glu Thr Phe Leu Asn Ile Ser Gln Met Asn Leu Ser Tyr Ser Glu
    210                 215                 220

Glu Glu Phe Asp Val Leu Ser Glu Ser Ala Val Asp Phe Ile Arg Thr
225                 230                 235                 240

Leu Leu Val Lys Lys Pro Glu Asp Arg Ala Thr Ala Glu Glu Cys Leu
                245                 250                 255

Lys His Pro Trp Leu
            260

<210> SEQ ID NO 6
<211> LENGTH: 261
<212> TYPE: PRT
<213> ORGANISM: Human

<400> SEQUENCE: 6

Ile Leu Thr Ser Lys Glu Leu Gly Arg Gly Lys Phe Ala Val Val Arg
  1               5                  10                  15

Gln Cys Ile Ser Lys Ser Thr Gly Gln Glu Tyr Ala Ala Lys Phe Leu
```

```
                20                  25                  30
Lys Lys Arg Arg Arg Gly Gln Asp Cys Arg Ala Glu Ile Leu His Glu
            35                  40                  45

Ile Ala Val Leu Glu Leu Ala Lys Ser Cys Pro Arg Val Ile Asn Leu
 50                  55                  60

His Glu Val Tyr Glu Asn Thr Ser Glu Ile Ile Leu Ile Leu Glu Tyr
 65                  70                  75                  80

Ala Ala Gly Gly Glu Ile Phe Ser Leu Cys Leu Pro Glu Leu Ala Glu
                85                  90                  95

Met Val Ser Glu Asn Asp Val Ile Arg Leu Ile Lys Gln Ile Leu Glu
            100                 105                 110

Gly Val Tyr Tyr Leu His Gln Asn Asn Ile Val His Leu Asp Leu Lys
            115                 120                 125

Pro Gln Asn Ile Leu Leu Ser Ser Ile Tyr Pro Leu Gly Asp Ile Lys
            130                 135                 140

Ile Val Asp Phe Gly Met Ser Arg Lys Ile Gly His Ala Cys Glu Leu
145                 150                 155                 160

Arg Glu Ile Met Gly Thr Pro Glu Tyr Leu Ala Pro Glu Ile Leu Asn
                165                 170                 175

Tyr Asp Pro Ile Thr Thr Ala Thr Asp Met Trp Asn Ile Gly Ile Ile
            180                 185                 190

Ala Tyr Met Leu Leu Thr His Thr Ser Pro Phe Val Gly Glu Asp Asn
            195                 200                 205

Gln Glu Thr Tyr Leu Asn Ile Ser Gln Val Asn Val Asp Tyr Ser Glu
            210                 215                 220

Glu Thr Phe Ser Ser Val Ser Gln Leu Ala Thr Asp Phe Ile Gln Ser
225                 230                 235                 240

Leu Leu Val Lys Asn Pro Glu Lys Arg Pro Thr Ala Glu Ile Cys Leu
                245                 250                 255

Ser His Ser Trp Leu
            260

<210> SEQ ID NO 7
<211> LENGTH: 29
<212> TYPE: PRT
<213> ORGANISM: Human

<400> SEQUENCE: 7

Asn Met Glu Lys Phe Lys Lys Phe Ala Ala Arg Lys Lys Trp Lys Gln
  1               5                  10                  15

Ser Val Arg Leu Ile Ser Leu Cys Gln Arg Leu Ser Arg
            20                  25

<210> SEQ ID NO 8
<211> LENGTH: 29
<212> TYPE: PRT
<213> ORGANISM: Human

<400> SEQUENCE: 8

Ser Lys Asp Arg Met Lys Lys Tyr Met Ala Arg Arg Lys Trp Gln Lys
  1               5                  10                  15

Thr Gly His Ala Val Arg Ala Ile Gly Arg Leu Ser Ser
            20                  25

<210> SEQ ID NO 9
<211> LENGTH: 29
<212> TYPE: PRT
```

```
<213> ORGANISM: Human

<400> SEQUENCE: 9

Thr Val Asp Cys Leu Lys Lys Leu Asn Ala Arg Arg Lys Leu Lys Gly
 1               5                  10                  15
Ala Ile Leu Thr Thr Met Leu Ala Thr Arg Asn Phe Ser
            20                  25

<210> SEQ ID NO 10
<211> LENGTH: 28
<212> TYPE: PRT
<213> ORGANISM: Human

<400> SEQUENCE: 10

Val Ser Glu Gln Ile Lys Lys Asn Phe Ala Lys Ser Lys Trp Lys Gln
 1               5                  10                  15
Ala Phe Asn Ala Thr Ala Val Val Arg His Met Arg
            20                  25

<210> SEQ ID NO 11
<211> LENGTH: 32
<212> TYPE: PRT
<213> ORGANISM: Human

<400> SEQUENCE: 11

Met Asp Thr Ala Gln Lys Lys Leu Gln Glu Phe Asn Ala Arg Arg Lys
 1               5                  10                  15
Leu Lys Ala Ala Val Lys Ala Val Val Ala Ser Ser Arg Leu Gly Ser
            20                  25                  30

<210> SEQ ID NO 12
<211> LENGTH: 28
<212> TYPE: PRT
<213> ORGANISM: Human

<400> SEQUENCE: 12

Gly Glu Asp Ser Gly Arg Lys Pro Glu Arg Arg Leu Lys Thr Thr
 1               5                  10                  15
Arg Leu Lys Glu Tyr Thr Ile Lys Ser His Ser Ser
            20                  25

<210> SEQ ID NO 13
<211> LENGTH: 20
<212> TYPE: DNA
<213> ORGANISM: Human

<400> SEQUENCE: 13
ggccggatga ggacctgagg                                              20

<210> SEQ ID NO 14
<211> LENGTH: 21
<212> TYPE: DNA
<213> ORGANISM: Human

<400> SEQUENCE: 14
tccacatccc accccagact c                                            21
```

DAP-KINASE RELATED PROTEIN

CROSS-REFERENCE TO RELATED APPLICATIONS

The present application is the national stage entry of international Application No. PCT/US99/13411, filed Jun. 15, 1999, which claims the benefit of Provisional Application No. 60/089,294, filed Jun. 15, 1998, the entire contents of which are hereby incorporated by reference. The present Application is also related to and hereby incorporates by reference the entire contents of application Ser. No. 08/810,712 filed Mar. 3, 1997 now U.S. Pat. No. 6,160,106 issued Dec. 12, 2000 and application Ser. No. 08/631,097, filed Apr. 12, 1996 now U.S. Pat. No. 5,968,816 issued Oct. 19, 1999.

BACKGROUND OF THE INVENTION

1. Field of the Invention

The present invention is directed to a DAP-kinase related protein.

2. Description of the Related Art

One of the factors which determines the proliferation state of cells is the balance between the growth-promoting effects of proto-oncogenes and the growth-constraining effects of tumor-suppressor genes. One mechanism by which tumor-suppressor genes exert their growth-constraining effect is by inducing a cell to undergo a physiological type of death. Such a controlled cell death is evident in a multitude of physiological conditions including metamorphosis, synaptogenesis of neurons, death of lymphocytes during receptor repertoire selection, and controlled homeostasis in the bone marrow and other proliferative tissues, etc. This cell death is regulated by the interaction of the cell with other cells or with cell products, for example through the activity of suitable cytokines.

Growth-inhibiting cytokines have a double effect on the target cell. They can either inhibit the proliferation of the cell and/or give rise to cell death. To date, blockage or activation of expression of known tumor-suppressor genes was shown to counteract or enhance, respectively, cytokines inhibition of cells growth (Kimchi, 1992) but did not have any effect on the death-promoting action of cytokines. For example, the growth inhibitory response to cytokines, such as TGF-β, was markedly reduced by the inactivation of the Rb gene, or the response to IL-6 was enhanced by introducing activated p53 genes (Pietenpol et al, 1990; Levy et al, 1993).

Apoptosis is a genetically controlled cell death process which is important in various developmental stages, as well as for cell maintenance and tissue homeostasis (Jacobson et al., 1997). During the last few years, many of the key players in this process have been identified, including receptors, adaptor proteins, proteases, and other positive and negative regulators (Green et al., 1998; White, 1996). One of the positive mediators of apoptosis, which has been cloned by the present inventors, is DAP-kinase (Deiss et al., 1995). This protein was discovered by a functional approach to gene cloning, based on transfections of mammalian cells with anti-sense cDNA libraries and subsequent isolation of death-protective cDNA fragments (Deiss et al., 1995; Deiss et al., 1991; Kimchi, 1998; Kissil et al., 1998; Levy-Strumpf et al., 1998). The anti-sense cDNA of DAP-kinase protected HeLa cells from interferon-gamma-induced cell death, and this property served as the basis for its selection.

DAP-kinase is a calcium/calmodulin-regulated 160 kDa serine/threonine protein kinase associated with actin microfilaments (Deiss et al., 1995; Cohen et al., 1997). Its structure contains at least two additional domains that might mediate interactions with other proteins: ankyrin repeats, and a typical death domain located at the C-terminal part of the protein (Deiss et al., 1995; Cohen et al., 1997). Overexpression of DAP-kinase in various cell lines results in cell death, and this death-promoting effect of DAP-kinase depends on at least three features: the catalytic activity, presence of the death domain, and the correct intracellular localization (Cohen et al., 1997; Cohen et al., 1999). Several independent lines of evidence proved that DAP-kinase is involved in apoptosis triggered by different external signals, including interferon-γ, TNF-α, activated Fas receptors, and detachment of cells from the extracellular matrix (Deiss et al., 1995; Cohen et al., 1997; Cohen et al., 1999; Inbal et al., 1997). A tumor suppressive function was recently attributed to the DAP-Kinase, coupling the control of apoptosis to metastasis (Inbal et al., 1997).

So far, only a few serine/threonine kinases were implicated in the regulation of programmed cell death, either as death-promoting and death-protecting proteins (Anderson, 1997; Bokoch, 1998). One such candidate is the JNK/SAPK (Basu et al., 1998). In one example, it was shown to mediate apoptosis induced by detachment from extracellular matrix (named anoikis) (Cardone et al, 1997). In this system, the JNK pathway is activated by MEKK-1, whose kinase activity is stimulated by caspase cleavage (Cardone et al., 1997). JNK may antagonize BCL-2 anti-apoptotic effects by phosphorylation (Park et al., 1997; Maundrell et al., 1997).

Another serine/threonine kinase is RIP, which like DAP-Kinase also possesses the death domain. RIP was shown to positively mediate apoptosis in cell cultures (Stanger et al., 1995). However, in vivo studies in RIP-deficient mice demonstrated its ability to exert anti-apoptotic effects by mediating the TNF-α-induced TNF-β activation (Kelliher et al., 1998). Other RIP members, RIP2 and RIP 3 were also recently identified and shown to possess pro-apoptotic effects (McCarthy et al., 1998; Sun et al., 1998; Yu et al., 1999).

Among the negative regulators of apoptosis is the protein kinase AKT. This protein was shown to phosphorylate BAD and thereby to prevent it from complexing and blocking the anti-apoptotic activity of BCL-$X_L$ (Datta et al, 1997; del Peso et al., 1997). AKT was also recently shown to phosphorylate pro-caspase-9, thus blocking its normal processing (Cardone et al., 1998).

Recently, the isolation and characterization of novel kinase members, homologous in their catalytic domains to DAP-kinase, was reported (Kawai et al., 1998; Kogel et al., 1998; Sanjo et al., 1998). One protein, named ZIP-kinase, was found to be 80% identical to DAP-kinase within the kinase domain, yet it lacks the CaM-regulatory domain and the other domains and motifs characteristic of DAP-kinase. Zip-kinase contains a leucine zipper domain at the C-terminus and is localized to the nucleus (Kawai et al., 1998; Kogel et al. 1998). The activation of ZIP kinase occurs by a different mechanism involving homo-dimerization, mediated by its leucine zipper domain. However, unlike DAP-kinase, ZIP-kinase is a nuclear protein, which instead of being regulated by a calmodulin-binding domain, is activated by homo-dimerization of its leucine-zipper motifs (Kogel et al., 1998). Another two less conserved nuclear proteins, DRAK1 and DRAK2, which are closely related to each other, and which share 50% identity with the kinase domain of DAP-kinase, were also recently characterized. Like ZIP-kinase, the DRAK1 and DRAK2 proteins also lack the CaM-regulatory domain. The overexpression of these two proteins in NIH3T3 cells induces some morphological changes associated with apoptosis, dependent on the functionality of their kinase domain (Sanjo et al., 1998). Together these kinases form a novel subfamily of serine/threonine kinases, as is evident from multiple sequence and phylogenetic analysis (Inbal et al., 1999).

Ectopic expression of the three wild type kinases, but not their catalytically inactive mutants, induced morphological changes characteristic of apoptosis (Kawai et al., 1998; Sanjo et al., 1998). Yet, in the case of ZIP-Kinase, these results are still controversial (Kogel et al., 1998).

Citation of any document herein is not intended as an admission that such document is pertinent prior art, or considered material to the patentability of any claim of the present application. Any statement as to the content or a date of any document is based on information available to the applicant at the time of filing and does not constitute an admission as to the correctness of such a statement

SUMMARY OF THE INVENTION

A new protein, DAP-Kinase-related 1 protein (DRP-1), which is a novel homologue of DAP-kinase, has been isolated. This novel calmodulin-dependent kinase is a 42 kDa serine/threonine kinase which shows a high degree of homology to DAP-kinase both in its catalytic domain and its calmodulin-regulatory region. The catalytic domain of DRP-1 is also homologous to recently identified ZIP-kinase and, to a lesser extent, to the catalytic domains of DRAK1/2.

DRP-1 is localized to the cytoplasm as shown by immunostaining and cellular fractionation assays. In vitro kinase assays indicate that wild type DRP-1, but not a kinase inactive mutant, undergoes autophosphorylation and phosphorylates an external substrate in a Ca2+/CaM-dependent manner. Ectopically expressed DRP-1 is able to induce apoptosis in various types of cells; with this killing being dependent on its kinase activity. The dominant negative form of DAP-Kinase (DAPk DD) is a potent blocker of apoptosis induced DRP-1. Thus, DRP-1 may be a death-promoting protein functioning in the biochemical pathway which involves DAP (death-associated protein)-kinase (e.g., forming a cascade of sequential kinases, one directly activating the other). Alternatively, the two kinases may operate to promote cell death in parallel pathways.

The present invention provides for a DRP-1 protein and functional homologues thereof having at least 85% sequence identity to the DRP-1 sequence of SEQ ID NO:2. Also provided is a fragment of DRP-1, which either is capable of inducing cell death or lacks such capability but instead is capable of inhibiting the activity of DRP-1 or a functional homologue thereof to induce cell death, and a homologous fragment which has at least 85% sequence identity thereto and which has the same properties.

The present invention further provides an isolated DNA molecule encoding for such DRP-1 protein, functional homologues thereof, or fragments thereof. Also included within the scope of the present invention are isolated DNA molecules which hybridize to the nucleotide sequence encoding DRP-1 protein under moderately or highly stringent conditions and encode a calmodulin-dependent serine/threonine kinase having the property of being capable of inducing cell death.

Other further aspects of the present invention include a composition comprising the DRP-1 protein, functional homologues and fragments thereof, and an antibody which specifically recognizes DRP-1 but does not cross-react with DAP kinase or ZIP kinase.

Yet another aspect of the present invention is directed to a single stranded RNA molecule complementary to at least a portion of the mRNA encoding the DRP-1 protein of SEQ ID NO:2. This single stranded antisense RNA molecule can be used in a method of neutralizing DRP-1 mRNA by hybridizing to the DRP-1 mRNA to prevent its translation into DRP-1 protein.

The present invention also provides a method for screening individuals for predisposition to cancer.

BRIEF DESCRIPTION OF THE DRAWINGS

FIG. 1 shows the nucleotide (SEQ ID NO:1) and amino acid (SEQ ID NO:2) sequence of the DAP-kinase homologue, DRP-1. The initiation (ATG) and stop (TAA) codons are boxed. The polyadenylation signal (ATTAAA) is underlined. The kinase domain and the calmodulin regulatory regions are in bold or underlined by a dash, respectively.

FIGS. 2A–2B show the multiple sequence alignment of the serine/threonine kinase domains (FIG. 2A) of the DAP-kinase-related proteins, DAP-kinase (SEQ ID NO:3), ZIP-kinase (SEQ ID NO:4), DRP-1 (corresponding to residues 13–275 of SEQ ID NO:2), DRAK1 (SEQ ID NO:5) and DRAK 2 (SEQ ID NO:6), conducted according to Hanks and Quinn (1991) with identical amino acids boxed and homologous amino acids shown with gray shading, and the multiple sequence alignment of the calmodulin regulatory regions (FIG. 2B) of DAP-kinase (SEQ ID NO:7), DRP-1 (corresponding to residues 292 to 320 of SEQ ID NO:2), smMLCK (SEQ ID NO:8), CaMKIIa (SEQ ID NO:9), CaMKI (SEQ ID NO:10), CaMKIV (SEQ ID NO: 11), and ZIP-Kinase (SEQ ID NO: 12) conducted manually, keeping the conserved (boxed) regions aligned to each other. The corresponding region of ZIP-Kinase which does not contain homology to DAP-Kinase and ZIP-Kinase CAM-regulatory regions is given at the bottom of FIG. 2B.

FIG. 3A shows Northern blot analysis of polyA+RNA extracted from various cell lines for mRNA expression of DRP-1, FIG. 3B show Western blot analysis of in vitro transcription and translation of DRP-1, and FIG. 3C shows protein expression of DRP-1 in HeLA cells on an immunoblot.

In FIG. 10B, pCDNA3²-luciferase is the negative control.

FIGS. 12A and 12B show by Western analysis that the C-terminal part of DRP-1 is required for its homo-dimerization. In FIG. 12A, wild type DRP-1 is shown to undergo specific homo-dimerization. The lanes correspond to the following co-transfections (5 μg of DRP-1 constructs and 20 μg of RFX1-ΔSmaI constructs/9 mm plate): (1) DRP-1-FLAG+RFX1-ΔSmaI-HA (control to rule-out nonspecific attachment of DRP-1 to HA beads or to an irrelevant gene). (2) RFX-ΔSmaI-FLAG+DRP-1-HA(control to rule out nonspecific attachment of DRP-1 to FLAG beads or to an irrelevant gene). (3) DRP-1–FLAG+DRP-1-HA. Both IP directions and their Western blottings are shown. In FIG. 12B, truncation of C-terminal 40 amino acids of DRP-1 is shown to abolish its homo-dimerization. The lanes correspond to the following co-transfections (5 μg of each construct/90 mm plate): (1) DRP-1-FLAG+DRP-1-HA (2) DRP-1-FLAG+DRP-1-Δ40-HA (3) DRP-1-FLAG+DRP-1-Δ73-HA (4) DRP-1-FLAG+DRP-1-Δ85-HA. The lower panel quantitate the immunoprecipitation efficiency of DRP-1-FLAG by the anti-FLAG antibodies.

DETAILED DESCRIPTION OF THE INVENTION

Figure 4A:
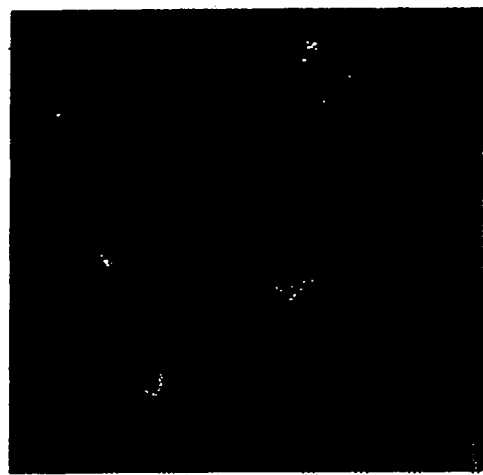
FIGS. 4A and 4B show control COS-7 cells and cellular localization of DRP-1 in COS-7 cells, respectively.

The present invention is based on the discovery by the present inventor of a novel serine/threonine kinase with remarkable homology to the catalytic and CaM-regulatory domains of DAP-kinase. This kinase, named DAP-kinase-related protein 1 (DRP-1), is a 42 kDa cytoplasmic protein which exhibits minor associations with insoluble matrix elements. The nucleotide (SEQ ID NO:1) and amino acid (SEQ ID NO:2) sequences of this DRP-1 protein are shown in FIG. 1. It is composed of 1742 nucleotides. The predicted initiation and stop codons are boxed, and the polyadenylation signal is underlined. The protein kinase domain is shown in bold letters and corresponds to amino acid residues 13 to 275 of SEQ ID NO:2. This protein displays 80% identity with the catalytic domain of DAP-kinase. The calmodulin-regulatory region is underlined with a dashed line; this region displays high homology to the corresponding region in DAP-kinase. The remainder of the C-terminal short part of the protein (the last 40 amino acid residues corresponding to residues 321 to 360 of SEQ ID NO:2) differs completely from DAP-kinase. Thus, DAP-kinase-related I protein does not carry all of the other motifs and protein modules characteristic of DAP-kinase. The mRNA expression levels transcribed from this gene are low.

Another protein, ZIP-kinase, which by virtue of its sequence homology to the kinase domain of DAP-Kinase, is also a member of the DAP-Kinase-related proteins subfamily, was recently identified (Kawai et al., 1998; Kogel et al., 1998). Unlike DAP-Kinase and DRP-1, ZIP-kinase is a nuclear protein, which instead of being regulated by a calmodulin-binding domain, is activated only by homo-dimerization via its leucine-zipper motifs (Kawai et al., 1998). To this group of kinases, another two less homologous nuclear proteins, DRAK1 and DRAK2, were recently added (Sanjo et al., 1998). Together they form a novel subfamily of serine/threonine kinases, as is evident from multiple sequence and phylogenetic analyses (Inbal et al., 1999). A multiple sequence alignment of the kinase domain of these serine/threonine kinases is shown in FIG. 2A.

To check the cellular functions of DRP-1, the laboratory of the present inventor overexpressed wild type DRP-1 in various cell lines and found that it induced apoptosis as measured by a few parameters. Unlike the wild type DRP-1, a kinase inactive mutant of DRP-1 (DRP-1 K42A), did not induce apoptosis, although it was expressed at a similar level in the transfected cells. In vitro kinase assays confirmed that DRP-1 K42A is indeed unable to phosphorylate MLC or under autophosphorylation. Also, a truncated form of DRP-1 which lacks the CaM-regulatory region, could be shown to induce very high levels of apoptosis, in a similar way to the analogous truncation of the CaM-regulatory region of DAP-Kinase (ΔCaM; Cohen et al., 1997). Such dependence on the catalytic activity for the apoptotic function is apparent also in the other members of DAP-kinase-related proteins (Kawai et al., 1998; Sanjo et al., 1998).

In a deletion mutant study, which is also presented in the Example herein, the existence of a positive element responsible for apoptotic induction which is located at the C-terminal part of DRP-1 is confirmed. This C-terminal tail of DRP-1 is also essential for its dimerization. Thus, self-dimerization is a requirement for the functionality of this kinase in apoptotic assays, although this property can be overridden by a further deletion of the CaM-regulatory region. Like DRP-1, ZIP-kinase-induced cell death is also controlled by its ability to undergo homo-dimerization via the C-terminal leucine zipper domain (Kawai et al., 1998). Three point mutations in the leucine zipper domain abolished the homo-dimerization as well as the ability of ZIP-kinase to undergo autophosphorylation in vitro and significantly reduced its ability to induce cell death of NIH 3T3 cells. It seems reasonable to assume that activation of these kinases is achieved by homo-dimerization followed by trans-phosphorylation events.

The high homology in the kinase domains of DAP-kinase and DRP-1, and the finding that they are both localized to the cytoplasm (either in soluble or insoluble forms), imply that they may share the same or closely related substrates. The phosphorylation sites for these kinases on the substrate may be either different or identical. Thus, these kinases may cooperate to induce apoptosis in the same cell type or, alternatively, function independently in different cell types, tissues or organs, or in response to different stimuli or time windows. Another possibility is that these kinases act sequentially along the same signaling pathway to induce apoptosis.

The present invention thus provides for the polypeptide of DRP-1 and for a calmodulin-dependent serine/threonine kinase homologue having the properties of DRP-1, such as the ability to phosphorylate protein in a calcium/calmodulin dependent manner and the ability to induce programmed cell death or apoptosis, and having at least 85% sequence identity to the amino acid sequence SEQ ID NO:2 of DRP-1. Preferably, the calmodulin-dependent serine/threonine kinase homologue has at least 90% sequence identity, and more preferably, at least 95% sequence identity to SEQ ID NO:2.

The term "sequence identity" as used herein means that the amino acid sequences are compared by alignment according to Hanks and Quinn (1991) with a refinement of low homology regions using the Clustal-X program. Such an amino acid alignment is shown in FIGS. 2A and 2B where the identical amino acid residues are presented in boxes (cutoff=50%) and homologous amino acid residues, determined according to the PAM 250 matrix, are presented by gray shading (cutoff=65%).

The Clustal-X program referred to in the previous paragraph is the Windows interface for the ClustalW multiple sequence alignment program (Thompson et al., 1994). The Clustal-X program is available over the internet at ftp://ftp-igbmc.u-strasbg.fr/pub/clustalx/. Of course, it should be understood that if this link becomes inactive, those of ordinary skill in the art can find versions of this program at other links using standard internet search techniques without undue experimentation. Unless otherwise specified, the most recent version of any program referred herein, as of the effective filing date of the present application, is the one which is used in order to practice the present invention.

If the above method for determining "sequence identity" is considered to be nonenabled for any reason, then one may determine sequence identity by the following technique. The sequences are aligned using Version 9 of the Genetic Computing Group's GDAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

In addition to the full length polypeptide of DRP-1 or a functional homologue thereto with at least 85% sequence identity, the present invention also provides for a fragment of the DRP-1 protein of SEQ ID NO:2 which either maintains the ability to induce cell death or lacks this ability but instead is capable of inhibiting the cell killing ability of DRP-1 protein or its functional homologue described above. It was unexpectedly discovered by the present inventor that the 40 amino acid C-terminal tail (residues 321 to 360 of SEQ ID NO:2) is critical to induction of cell death. As the action of DRP-1 is dependent on dimerization, the 40 amino acid tail, by itself, can inhibit the ability of DRP-1 to induce cell death by interfering with and preventing DRP-1 from dimerizing. Furthermore, it was also unexpectedly discovered that the catalytic domain, by itself (without the calmodulin regulatory domain and the 40 amino acid C-terminal tail, e.g., amino acid residues 13 to 275 of SEQ ID NO:2), is super-killing. One of ordinary skill in the art can readily obtain fragments of the full length sequence of the present invention using N-terminal amino peptidases or C-terminal carboxypeptidases. Each fragment can then be readily tested to see if it possesses one of the two functions described herein for such fragments, without undue experimentation.

Besides fragments of DRP-1 having the above-mentioned properties, fragments having an amino acid sequence with at least 85% sequence identity to the above fragments of DRP-1, preferably with at least 90% sequence identity, and more preferably with at least 95% sequence identity, and maintaining the cell death induction or inhibition properties of the original fragment, are also comprehended by the present invention.

Also comphrended by the present invention are chemical derivatives of the DRP-1 and functional homologues and fragments thereof, as defined above, where a "chemical derivative" contains additional chemical moieties not normally part of the DRP-1 amino acid sequence. Covalent modifications of the amino acid sequence are included within the scope of this invention. Such modifications may be introduced into DRP-1 or fragments thereof by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters, such as methyl picolinimidate, pyridoxal phosphate, pyridoxal, chloroborohydride, trinitrobenzenesulfonic acid, O-methyliosurea, 2,4-pentanedione, and transaminase-catalyzed reaction with glyoxylate.

Arginyl residues are modified by reaction with one or several conventional reagents, among them phenylglyoxal, 2,3-butanedione, and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and e-nitro derivatives, respectively.

Carboxyl side groups (aspartyl or glutamyl) are selectively modified by reaction with carbodiimides (R'N—C—N—R') such as 1-cyclohexyl-3-[2-morpholinyl-(4-ethyl)] carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

The present invention also comprehends an isolated DNA molecule which includes a nucleotide sequence encoding the DRP-1 protein of SEQ ID NO:2, a functional homologue thereof as described above, or a fragment of DRP-1 which either maintains the ability of DRP-1 to induce cell death or lacks this ability but is instead capable of inhibiting the cell killing ability of DRP-1 protein, as defined above. The isolated DNA molecule according to the present invention is also intended to comprehend a DNA molecule which hybridizes under moderately stringent, preferably highly stringent, conditions to the nucleotide sequence encoding DRP-1 (corresponding to nucleotides 62 to 1141 of SEQ ID NO:1) and which encodes a polypeptide which maintains the cell death induction properties of DRP-1. The present invention further comprehends isolated DNA molecules which hybridize under moderately stringent, preferably highly stringent, conditions to a nucleotide sequence which encodes for a fragment of DRP-1 which either maintains the ability of DRP-1 to induce cell death (i.e., nucleotides 98 to 886 of SEQ ID NO:1 encoding the catalytic kinase domain of DRP-1) or lacks the ability but is instead capable of inhibiting the cell killing ability of DRP-1 protein (i.e., nucleotides 1022 to 1141 of SEQ ID NO:1 encoding the 40 amino acid C-terminal tail of DRP-1). Furthermore, polypeptides encoded by any nucleic acid, such as DNA or RNA, which hybridizes to the nucleotide sequence of nucleotides 62 to 141 of SEQ ID NO:1 under moderately stringent or highly stringent conditions are considered to be within the scope of the present invention as long as the encoded polypeptide maintains the ability of DRP-1 to induce cell death.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA—DNA hybrid:

$$Tm = 81.5°\ C. + 16.6(\text{Log}M) + 0.41(\%\ GC) - 0.61(\%\ \text{form}) - 500/L$$

where M is the molarity of monovalent cations, % GC is the percentage of G and C nucleotides in the DNA, % form is the percentage of formamide in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 100% hybrid according to the equation of Meinkoth, hybridization will occur even if there is up to about 10% mismatch.

As used herein, "highly stringent conditions" are those which provide a Tm which is not more than 10° C. below the Tm that would exist for a perfect duplex with the target sequence, either as calculated by the above formula or as actually measured. "Moderately stringent conditions" are those which provide a Tm which is not more than 20° C. below the Tm that would exist for a perfect duplex with the target sequence, either as calculated by the above formula or as actually measured. Without limitation, examples of highly stringent (5–10° C. below the calculated or measured Tm of the hybrid) and moderately stringent (15–20° C. below the calculated or measured Tm of the hybrid) conditions use a wash solution of 2×SSC (standard saline citrate) and 0.5% SDS (sodium dodecyl sulfate) at the appropriate temperature below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE (standard seline-phosphate-EDTA)), 5× Denhardt's reagent, 0.5% SDS, 100 µg/ml denatured, fragmented salmon sperm DNA at a temperature approximately 20° to 25° C. below the Tm. If mixed probes are used, it is preferable to use tetramethyl ammonium chloride (TMAC) instead of SSC (Ausubel, 1987, 19989.

Additional aspects of the present invention are vectors which carry the isolated DNA molecule according to the present invention and a host cell which is transformed with the isolated DNA according to the present invention.

The present invention further provides for antisense RNA complementary to at least a portion of a messenger RNA (mRNA or "sense" RNA) molecule which is the transcription product of the DNA sequence encoding the DRP-1 protein of SEQ ID NO:2. The antisense DRP-1 sequence can be chemically synthesized or it can be expressed in host cells. However, when expressed in host cells, the expressed antisense RNA must be stable (i.e., does not undergo rapid degradation). Moreover, the antisense DRP-1 RNA, will essentially specifically only hybridize to the sense DRP-1 mRNA and form a stable double-stranded RNA molecule that is essentially non-translatable. In other words, the antisense DRP-1 RNA prevents the expressed sense DRP-1 mRNA from being translated into active DRP-1 protein. When expressed in host cells, a vector-borne antisense DRP-1 sequence may carry either the entire DRP-1 gene sequence or merely a portion thereof as long as the antisense DRP-1 sequence is capable of hybridizing to "sense" DRP-1 mRNA to prevent its translation into DRP-1 protein. Accordingly, an "antisense" sequence of the present invention can be defined as a sequence which is capable of specifically hybridizing to "sense" DRP-1 mRNA to form a non-translatable double-stranded RNA molecule.

The antisense DRP-1 sequence need not hybridize to the entire length of the DRP-1 mRNA. Instead, it may hybridize to selected regions, such as the 5'-untranslated sequence, the coding sequence, or the 3'-untranslated sequence of the "sense" mRNA. In view of the size of the mammalian genome, the antisense DRP-1 sequence is preferably at least 17, more preferably at least 30, base pairs in length. However, shorter sequences may still be useful, i.e., they either fortuitously do not hybridize to other mammalian sequences, or such "cross-hybridization" does not interfere with the metabolism of the cell in a manner and to a degree which prevents the accomplishment of an object of this invention. The greater the length of the antisense sequence and the greater the number of complementary base pairs, the greater the number of non-complementary bases that can be tolerated, especially if the non-complementary bases are scattered. Both the preferred hybridization target on DRP-1 and the preferred antisense sequence length are readily determined by systematic experiment.

Standard methods such as described in Sambrooke et al., (1989) can be used to systematically remove an increasingly larger portion of the antisense DRP-1 sequence from a plasmid vector. Besides the full length antisense DRP-1 sequence, a series of staggered deletions may be generated, preferably at the 5'-end of the antisense DRP-1 sequence. This creates a set of truncated antisense DRP-1 sequences that still remain complementary to preferably the 5'-end of the sense DRP-1 mRNA and as a result, still forms a RNA molecule that is double-stranded at the 5'-end of the sense DRP-1 mRNA (complements the 3'-end of an antisense DRP-1 RNA) and remains non-translatable.

The antisense RNA according to the present invention can be used in a method to neutralize a mRNA molecule, which is the transcription product of the DNA sequence encoding the DRP-1 protein of SEQ ID NO:2, by allowing the antisense RNA to hybridize to the DRP-1 mRNA to prevent its translation into DRP-1 protein.

A further aspect of the present invention is directed to a composition, such as a pharmaceutical composition, which contains DRP-1, functional homologues or fragments thereof and a pharmaceutically-acceptable excipient, carrier, diluent, or auxiliary agent.

An antibody, which specifically recognizes DRP-1 or functional homologues thereof is part of the present invention as long as the antibody does not cross-react with DAP-Kinase or ZIP-kinase. For instance, an antibody that specifically recognizes the unique 40 amino acid C-terminal tail of DRP-1, which is not present in DAP-Kinase or ZIP-kinase, is a preferred embodiment of the antibody according to the present invention. Such an antibody can be used for diagnostic imaging, purification of DRP-1 etc.

The terms "antibody" or "antibodies" as used herein are intended to include intact antibodies, such as polyclonal antibodies or monoclonal antibodies (mAbs), as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (Eshhar et al., 1990; Gross, et al., 1989). Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked $V_H$-$V_L$ or single chain $F_V$). Both $V_H$ and $V_L$ may copy natural monoclonal antibody sequences or one or both of the chains may comprise a CDR-FR construct of the type described in U.S. Pat. No. 5,091,513 (the entire contents of which are hereby incorporated herein by reference). The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are hereby incorporated herein by reference.

As mentioned above, the terms "antibody" or "antibodies" are also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., 1983). It will be appreciated that Fab and F(ab')$_2$ and other fragments of the antibodies useful in the present invention may be used for the detection and quantitation of DRP-1 or functional homologues thereof according to the methods used for intact antibody molecules. Such fragments are typically produced by proteolytic cleavage, using enzymes such as papain (to produce Fab fragments) or pepsin (to produce F(ab)$_2$ fragments).

The present invention comprehends not only the intact antibodies or fragments, but also any molecule which includes an antigen binding portion of an antibody such that the molecule is capable of binding to the antigen. It is well within the skill of the art for the artisan to make e.g., fusion proteins which include antigen binding portions of an antibody fused to any other material which is desired to be carried to the antigen binding site, such as marker molecules, toxins, etc.

The antibodies, or fragments of antibodies, of the present invention may be used to quantitatively or qualitatively detect the presence of DRP-1 or functional homologues according to the present invention in a sample. The antibody according to the present invention may also be used for the isolation and purification of DRP-1 or homologues and fragments thereof, such as in an affinity column where the antibodies are immobilized on a solid phase support or carrier.

By "solid phase support or carrier" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

One of the ways in which the DRP-1-specific antibody can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. The detection can be accomplished by to calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect DRP-1 protein through the use of a radioimmunoassay (RIA) (Chard, T., "An Introduction to Radioimmune Assay and Related Techniques" (In: Work, T. S., et al., *Laboratory Techniques in Biochemistry in Molecular Biology*, North Holland Publishing Company, New York (1978), incorporated by reference herein). The radioactive isotope can be detected by such means as the use of a gamma counter or a liquid scintillation counter or by autoradiography. Radioactively labeled antibodies or antibody fragments can also be used for their capacity to kill cells bound by such antibodies, or cells in the immediate vicinity which are exposed to the radiation from such antibodies. It is also possible to label the antibody with a fluorescent compound, a chemiluminescent or bioluminescent compound.

The antibody molecules of the present invention may also be adapted for utilization in an immunometric assay (also known as a "two-site" or "sandwich" assay) which is well know in the art.

In the present specification, the term "programmed cell death" is used to denote a physiological type of cell death which results from activation of some cellular mechanisms, i.e., death which is controlled by the cell's machinery. Programmed cell death may, for example, be the result of activation of the cell machinery by an external trigger, e.g., a cytokine, which leads to cell death. The term "apoptosis" is also used interchangeably with programmed cell death.

The term "tumor" in the present specification denotes an uncontrolled growing mass of abnormal cells. This term includes both primary tumors, which may be benign or malignant, as well as secondary tumors, or metastases, which have spread to other sites in the body.

DRP-1 can be used to inhibit growth and metastasis of tumors. Tumor cells are exposed to a variety of death-inducing signals which, in combination with DAP-kinase-related I, can lead to death of the tumor cells. For example, in the blood stream, invading tumor cells must resist programmed cell death that is induced by interactions with cytotoxic T lymphocytes, natural killer cells, and macrophages, and with the cytokines which these hematopoietic cells secrete (e.g., IFNs, TNF, IL-1β). Tumor cells must also resist the apoptotic cell death induced by nitric oxide anions produced by the endothelial cells, and withstand mechanical shearing forces caused by hemodynamic turbulence. Moreover, during the intravasation or extravasation processes, and during growth in a foreign hostile microenvironment, locally produced inhibitory cytokines (e.g., TGF-β or loss of cell-matrix interactions (e.g., detachment from the basement membranes) also trigger apoptotic cell death.

DRP-1 is useful in promoting death of tumor cells. The protein may be administered to patients, in particular, to cancer patients, which administration may cause death of the tumor cells. The protein may be administered per se, or may be administered by an expression vector comprising a DNA molecule of the present invention.

Because DRP-1 displays 80% identity with the catalytic domain of DAP-kinase and has a region which displays a high homology to the calmodulin-regulatory region of DAP-kinase, it is expected that DRP-1 has enzymatic kinase activity, which is calmodulin-dependent. Thus, DRP-1 has use as an enzyme and may be used, for example, as the enzyme in any in vitro enzymatic reaction which requires the presence of a kinase enzyme. Accordingly, DRP-1 can be used in vitro to catalyze phosphorylation reactions as a kinase.

DRP-1 is capable of inducing apoptotic cell death when overexpressed in various cell lines. This ectopic cell death is blocked specifically by the death domain of DAP-kinase, suggesting possible crosstalk between these two kinases. Thus, DRP-1 may also be used for promoting the death of normal or tumor cells and for suppressing the metastatic activity of tumor cells. A particular application of the death-promoting aspect is in therapy of diseases or disorders associated with uncontrolled, pathological cell growth, e.g., cancer (primary tumors and metastasis), psoriasis, autoimmune disease and others. Indeed, it is expected that the DAP-kinase-related protein I of the present invention and DNA encoding it, may be used in the same manner as disclosed in detail in U.S. application Ser. Nos. 08/810,712 and 08/631,097, as well as WO 95/10630.

According to a further aspect of the present invention, referred to herein at times as "the screening aspect", DRP-1 DNA molecules are used in order to screen individuals for predisposition to cancer. In accordance with this aspect the screening is carried out by comparing the sequence of each of the DAP-kinase-related I DNA molecules to each of the respective DAP genes in the individual, or by following RNA and/or protein expression. The absence of a DAP-kinase-related I gene, a partial deletion or any other difference in the sequence that indicates a mutation in an essential region, or the lack of a DRP-1 RNA and/or protein which may result in a loss of function may lead to a predisposition for cancer. For screening, preferably a battery of related DAP and DRP-1 genes maybe used, as well as different antibodies.

In the screening aspect, DAP-kinase related product I molecules may also be used for prognostic purposes. For example, if a tumor cell lacks DRP-1 activity, this may reflect high chances of developing metastasis. In addition, DRP-1 positive cells may be more susceptible to control by chemotherapeutic drugs that work by inducing apoptosis, so that the choice of treatment modalities may be made based upon the DRP-1 state of the cells.

The DAP-kinase-related product can be used to screen individuals for predisposition to cancer. There is provided a method for detecting the absence of a DRP-1 gene, a partial deletion or a mutation (i.e., point mutation, deletion or any other mutation) in the DRP-1 genes of an individual, or the absence of a DRP-1 RNA or protein, comprising probing genomic DNA, cDNA, or RNA from the individual with a DNA probe or a multitude of DNA probes having a complete or partial sequence of the DRP-1 genes, or probing protein extracts with specific antibodies.

A particular application of the screening aspect of this invention is in the screening for individuals having a predisposition to cancer, an absence of the gene, or a detected mutation or deletion indicating that the individual has such a predisposition.

One example of a method in accordance with the screening aspect typically comprises the following steps:
(a) obtaining a sample of either genomic DNA from cells of the individual or cDNA produced from mRNA of said cells;
(b) adding one or more DNA probes, each of said probes comprising a complete or partial sequence of a DRP-1 gene;
(c) providing conditions for hybridization to determine whether the DRP-1 gene is present or absent, i.e., whether there is a match between the sequence of the DNA probe or probes and a sequence in the DNA of said sample or a mismatch, a mismatch indicating a deletion or a mutation in the endogenous DNA and a predisposition to cancer in the tested individual.

Other examples of the screening aspect of the invention are well known to the skilled artisan and include, but are not limited to, Northern blots, RNase protection assays, and various PCR procedures.

The mutation in the DRP-1 gene, indicating a possible predisposition to cancer, can also be detected by the aid of appropriate antibodies which are able to distinguish between a mutated, a non-functional and a normal functional DRP-1 gene product. In addition, mutations that abolish protein translation or transcription due to promoter inactivation can be detected with the aid of antibodies that are used to react with protein cell extracts. Screening is also possible with respect to metastases.

Having now generally described the invention, the same will be more readily understood through reference to the following example which is provided by way of illustration and is not intended to be limiting of the present invention.

EXAMPLE

In this study, the identification and the structure/function analysis of a novel DAP-kinase-related protein, DRP-1, is described, DRP-1 is a 42 kDa $Ca^{2+}$/CaM-regulated serine/threonine kinase which shows high degree of homology to DAP (Death Associated Protein)-kinase. The homology spans over the catalytic domain and the calmodulin-regulatory region, whereas the rest C-terminal part of the protein differs completely from DAP-kinase and displays no homology to any known protein. The catalytic domain is also homologous to the recently identified ZIP-kinase and to a lesser extent to the catalytic domains of DRAK1/2, thus forming together a novel subfamily of serine/threonine kinases. DRP-1 is localized to the cytoplasm as shown by immunostaining and cellular fractionation assays. In vitro kinase assays indicate that wild type DRP-1, but not a kinase inactive mutant, undergoes autophosphorylation and phosphorylates an external substrate in a $Ca^{2+}$/CaM-dependent manner. Ectopically expressed DRP-1 is able to induce apoptosis in various types of cells. Cell killing by DRP-1 is dependent on two features: the intact kinase activity and the presence of C-terminal 40 amino acids shown to be involved in self-dimerization of the kinase. Interestingly, further deletion of the CaM-regulatory region overrided the indispensable role of the C-terminal tail and generated a "superkiller" mutant. Finally, a dominant negative fragment of DAP-kinase encompassing the death domain is a potent blocker of apoptosis induced by DRP-1. This implies a possible functional connection between DAP-kinase and DRP-1. The experiments conducted in this study and the results obtained are presented below.

Materials and Methods cDNA Cloning and Northern Blot Analysis

A PCR fragment of 364 bp was obtained from a λgt11 human spleen cDNA library (Clontech) using primers from the deduced DRP-1 sequence, 1047-GGCCGGATGAG-GACCTGAGG-1066 (SEQ ID NO:13) and 1411-TCCA-CACTCCCACCCCAGACTC-1390 (SEQ ID NO:14). To obtain the full length cDNA of DRP-1, the same cDNA library was screened with the radiolabeled PCR product. Positive phage clones were isolated, cDNA was subcloned into a BlueScript vector and analyzed by restriction enzyme mapping and DNA sequencing. A 270 bp 3'-fragment from the full length cDNA of DRP-1 was generated by EcoRI digestion, and used to probe polyA+ RNA prepared by a standard procedure from various cell lines.

In Vitro Transcription and Translation Assay

The full length cDNA was used as a template for in vitro transcription from the T7 promoter. This RNA was translated in reticulocyte lysate (TNT® T7 Quick Coupled Transcription/Translation System; Promega) by conventional procedures, with [$^{35}$S] methionine (Amersham) as a labeled precursor. The reaction product was then run on 12% SDS-PAGE gel, followed by sodium salicylate incubation for signal amplification. The gel was dried and exposed to X-ray film.

In vitro Kinase Assay 293 cells were transfected by a FLAG-tagged wild type DRP-1, DRP-1 K42A mutant, or mock-transfected. Cell lysates of 293 transfected cells were prepared as previously described (Deiss et al., 1995). Immunoprecipitation of DRP-1 or DRP-1 K42A mutant from 150 µg total extract was done with 20 µl anti-FLAG M2 gel (IBI, Kodak) in 500 µl of PLB supplemented with protease and phosphatase inhibitors for 2 h at 4° C. Following three washes with PLB, the immunoprecipitates were washed once with reaction buffer (50 mM HEPES pH 7.5, 20 mM $MgCl_2$, and 0.1 mg/ml BSA). The proteins bound to the beads were incubated for 15 min at 30° C. in 50 µl of reaction buffer containing 15 µCi [γ32p] ATP (3 pmole), 50 µM ATP, 5 µg MLC (Sigma), and where indicated, also 1 µM bovine calmodulin (Sigma), 0.5 mM $CaCl_2$, or 3 mM EGTA in the absence of calmodulin/$CaCl_2$. Protein sample buffer was added to terminate the reaction, and after boiling, the proteins were analyzed on 11% SDS-PAGE. The gel was blotted onto a nitrocellulose membrane and $^{32}$P_labeled proteins were visualized by autoradiography.

Immunostaining of Cells

DRP-1 transfected or mock-transfected COS-7 cells were plated on glass cover-slips (13 mm diam.). After 48 hours, the cells were fixed/permeabilized in 3% formaldehyde for 5 min, methanol 5 min, acetone 2 min. The cells were blocked in 10% NGS for 30 min and incubated with anti-FLAG antibodies (dilution 1:100; IBI, Kodak) in 10% NGS for 60 min. Rhodamine-conjugated goat anti-mouse secondary antibodies (dilution 1:200; Jackson Immuno Research Lab.) and the nucleic acid dye, Oligreen (dilution 1:5000; Molecular Probes), for nuclear staining were then applied. The coverslips were mounted in Mowiol and observed under fluorescence microscope.

Detergent Extraction Assay

Sub-confluent cultures of COS-7 transfected cells, grown on 9 cm plate, were washed once with PBS and then with MES buffer (50 mM MES pH 6.8, 2.5 mM EGTA, 2.5 mM $MgCl_2$). The cells were extracted for 3 min with 0.5 ml of 0.5% Triton X-100 in MES buffer supplemented with protease inhibitors. The supernatant (the soluble fraction-Sol) was collected, centrifuged for 2 min. at 16,000x g at 4° C., and the clear supernatant was then transferred to new tubes. Two volumes of cold ethanol were added and the tubes were incubated at −20° C. for overnight, centrifuged 10 min. at 16,000x g at 4° C. and resuspended in 200 µl of 2x protein sample buffer without dye. The detergent insoluble matrix (InSol) remaining on the plate was extracted in 200 µl of 2x protein sample buffer, scraped from the plate with rubber policeman and collected into tube. The samples were loaded on 10% SDS-PAGE, 100 µg protein extracts were loaded on each lane from the Sol fraction, equivalent volumes of InSol were loaded. Analysis of the proteins was done using monoclonal anti-FLAG antibodies (dilution 1:200; IBI, Kodak).

Cell Lines, Transfections and Apoptotic Assays

All cell lines were grown in DMEM (Biological Industries) supplemented with 10% fetal calf serum (Bio-Lab). For transient transfection, 1×10$^5$ cells per well, were seeded in a 6 well plate a day before transfection. Transfections were done by calcium-phosphate method. For cell death assays by inducing overexpression, a mixture containing 1.5 µg of cell death plasmid (expressing either DRP-1 or ΔCaM DAPk mutant) and 0.5 µg of pEGFP-NI plasmid (Clontech) was used. For cell death protection assays we used a mixture containing 1.2 µg of cell death inducing plasmid (either DRP-1 or ΔCaM DAPk mutant), 0.5 µg of a plasmid to be tested for cell death protection (expressing DAPk-DD, DN FADD or luciferase as negative control), and 0.5 µg of pEGFP-NI plasmid. Cells were counted and photographed 24 hours after transfection. In each transfection, three fields, each consisting of at least 100 GFP-positive cells, were scored for apoptotic cells according to their morphology. When indicated, cell lysates were prepared from the transient transfection at 24 hours, for protein analysis. The transfections of Rat embryo fibroblasts (REF) and FACS analysis of transfected fibroblasts for DNA content distribution were done as previously described (Kissil et al., 1998).

Co-Immunoprecipitation Assays 293 cells grown in 90 mm plates (1×10$^6$ cells/plate) were co-transfected with 5 µg FLAG-tagged or HA-tagged DRP-1 and 20 µg of HA-tagged or FLAG-tagged RFX1ΔSmaI, respectively, or with DRP-1-HA and DRP-1-FLAG, 5 µg each. Immunoprecipitation of DRP-1 or RFX1-ΔSmaI from 1 mg total extract was done using anti-FLAG M2 gel or anti-HA as described above. Detection of bound proteins was done using anti-HA antibodies (dilution 1:1000, Babco) or anti-FLAG antibodies. For the deletion mutant study, 5 µg of FLAG-tagged fully length DRP-1 were co-transfected with 5 µg of HA-tagged DRP-1 deletion mutants. Immunoprecipitation of DRP-1 from 1 mg total extract was done using anti-FLAG M2 gel as described above. Detection of co-immunoprecipitated proteins (the mutants of DRP-1 or full length DRP-1) was done using anti-HA antibodies.

Nucleotide Sequence Accession Number

The nucleotide sequence of human DRP-1 has been submitted to the GenBank™/EBI Data Bank (accession no. AF052941). The murine DRP-1 is also deposited at the GenBank™/EBI Data Bank (accession no. AF052942).

Results

Cloning of DRP-1 To identify proteins that share homologous sequences with DAP-kinase, EST databases were searched using the BLAST™ program. Two ESTs of human and murine origin showed remarkable amino acid homology to the catalytic domains of DAP-kinase and the recently identified protein ZIP-kinase (79.5% and 80.2% identity, respectively). A second EST search was performed using the 5' and the 3' ends of the human EST, which identified a few more overlapping ESTs. A putative novel cDNA sequence was generated and used to design primers for cloning the full length cDNA. PCR performed on human spleen cDNA library amplified a 364 bp fragment that was further used to screen the same library. The full length cDNA was then isolated, subcloned into BlueScript vector, and sequenced.

The isolated cDNA was found to be 1742 bp long and to contain a serine/threonine kinase domain with all of the 12 characterized subdomains present (Park et al., 1997, FIG. 1A). Sequence alignment indicated that the catalytic domain of DRP-1 has 80% sequence identity to that of DAP-kinase and ZIP-kinase, yet less 50% sequence identity to the newly identified DRAK proteins (FIG. 2A). Like DAP-kinase but unlike ZIP-kinase, DRP-1 carries a typical CaM-regulatory region adjacent to its catalytic domain, as shown in FIGS. 1 and 2B. As compared with other kinases such as CaKIIa and MLCK, DRP-1 has the highest homology to DAP-kinase in this region, as shown in FIG. 2B. The remaining short stretch of amino acids at the C-terminal part of DRP-1 (40 amino acid tail) displays no homology to any known protein.

Expression of DRP-1 and Tissue Distribution

To check the RNA expression of DRP-1, polyA+RNA was prepared from various cell lines and hybridized to a probe designed from the less conserved region of DRP-1. A single weak band of 1.9 kb appeared in some cell lines, in a Northern blot analysis of poly A+RNA (3 micrograms) extracted from various cell lines (FIG. 3A), suggesting that the mRNA is expressed at low amounts in HeLa, 293 and MCF-7 cells. The mRNA was hybridized with a radiolabeled human DRP-1 probe. The position of the transcript is indicated by an arrow. From PCR analysis of various cDNA libraries and the data gathered from EST searches, it was concluded that human DRP-1 is expressed, at least, in spleen, colon, breast, and leukocyte tissue.

In vitro transcription and translation assays conducted in reticulocyte lysates using the cloned DRP-1 cDNA as a template generated a single protein band of about 42 kDa in size, as predicted by its sequence. This protein band, obtained by Western blot analysis of in vitro transcribed and then translated DRP-1, is shown in FIG. 3B. A FLAG-tagged DRP-1 was then cloned into pCDNA3 vector and expressed in HeLa cells. A protein of 42 kDa was evident upon immunoblot analysis of the cell lysates with anti-FLAG antibodies, shown in FIG. 3C. In this case, 24 hours following transfection, the cells were harvested and lysed. The extracted proteins were separated by SDS-PAGE and then immunoblotted with anti-FLAG antibodies.

Cellular Localization of Ectopically Expressed DRP-1

Figure 4B:
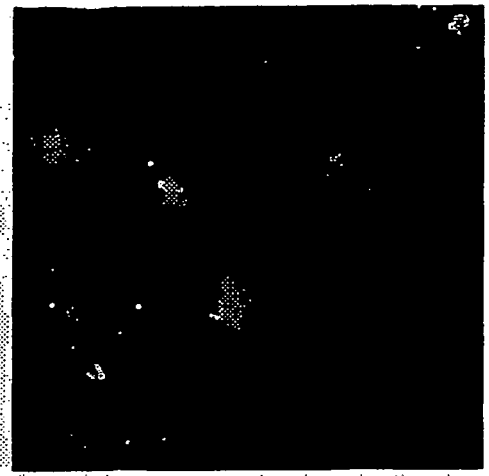

In order to follow the cellular localization of the exogenous DRP-1, FLAG-tagged DRP-1 was expressed in COS-7 cells. COS-7 cells were transfected by a FLAG-tagged DRP-1 cloned in pCDNA3 vector, fixed and permeabilized in 1% formaldehyde followed by methanol/acetone treatment. Cells were visualized under fluorescence microscope. Immunoblot analysis proved that DRP-1 was expressed in these cells. For the immunostaining procedure, the non-transfected (FIG. 4A) and DRP-1 transfected (FIG. 4B) COS-7 cells were then fixed and reacted both with Oligreen for nuclear staining and anti-FLAG antibodies for DRP-1 staining. Specific DRP-1 staining was detected in the cytoplasm of these cells, as shown in FIG. 4B.

Figure 4C:
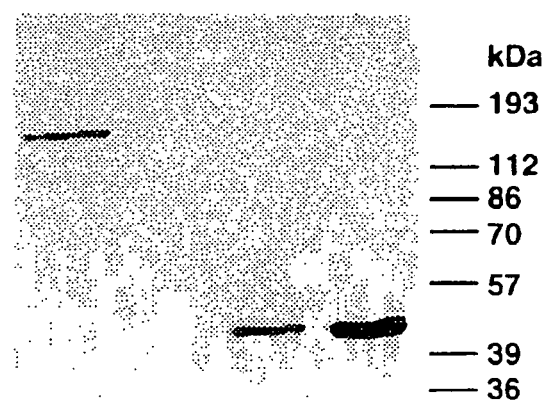
FIG. 4C shows a Western blot of fractions from a detergent extraction of COS-7 cells transfected with a pcDNA3 vector expressing either FLAG-tagged DRP-1 or DAP-Kinase.

A gentle cell extraction was performed with nonionic detergent, 0.5% TRITON X-100, that removes lipids and soluble proteins, leaving intact the detergent insoluble matrix composed of the nucleus, the cytoskeleton framework, and cytoskeleton-associated proteins. In contrast to DAP-kinase, which is exclusively localized to the cytoskeleton, and hence found only in detergent insoluble fractions (Cohen et al., 1997, FIG. 4C), DRP-1 was preferentially eluted from the detergent soluble fraction, while a small amount was eluted from the insoluble fraction, as shown in FIG. 4C. Thus, it was concluded that DRP-1 is a cytoplasmic protein with minor association with insoluble matrix components.

Intrinsic Kinase Activity of DRP-1

To test whether DRP-1 functions as a kinase as predicted from the amino acid sequence, an in vitro kinase assay was performed using myosin light chain (MLC) as an exogenous substrate. This substrate was chosen because it is phosphorylated by DAP-kinase (Cohen et al., 1997). DRP-1 was transfected into human kidney 293 cells, immunoprecipitated, and incubated with MLC in the presence and absence of Ca2+ and calmodulin. Both MLC phosphorylation and DRP-1 autophosphorylation were evident, as can be seen from FIG. 5A.

Figure 5A:
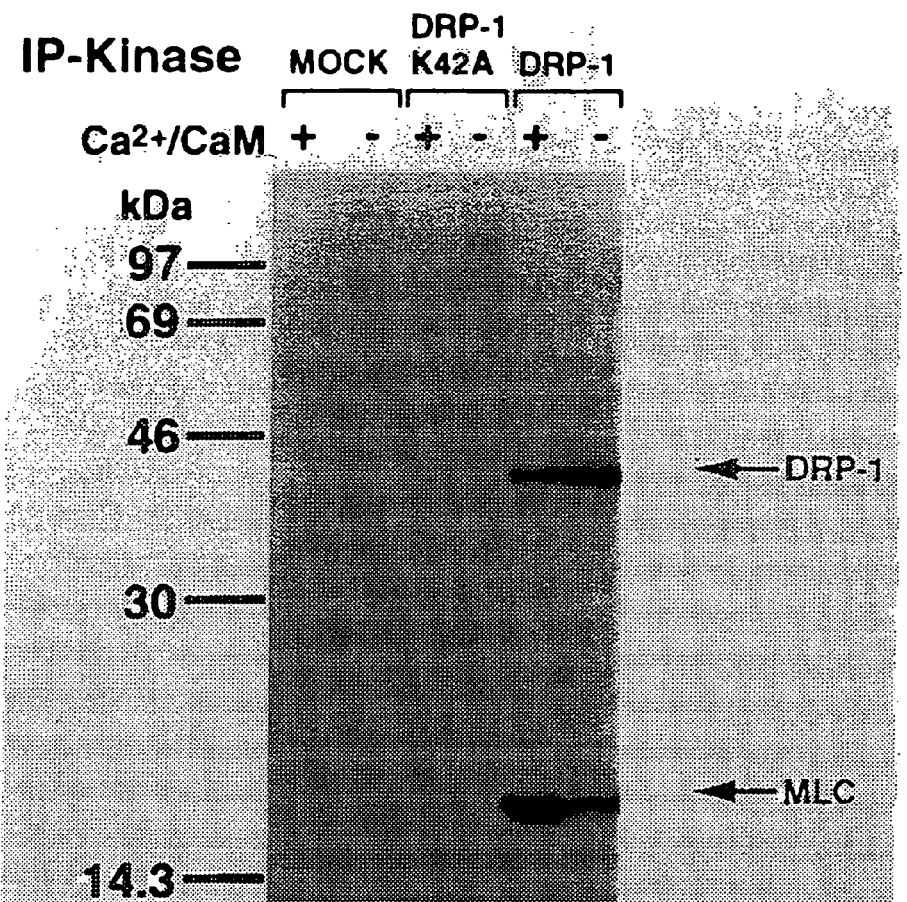
FIG. 5A shows in vitro kinase activity of DRP-1 and FIG. 5B shows a Western blot of DRP-1 proteins.
Figure 5B:
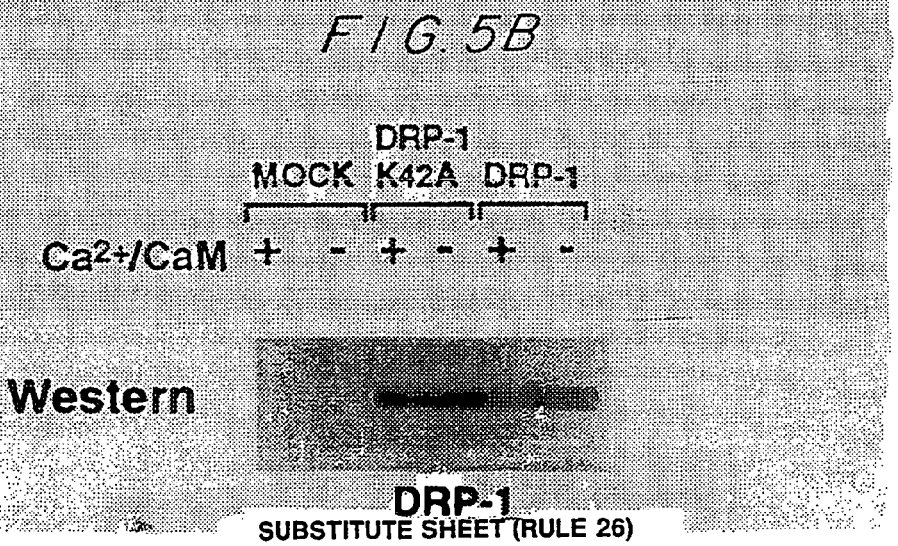

In assaying the in vitro kinase activity of DRP-1, the proteins were assayed in the presence or absence of CA2+/CaM and MLC. The proteins were run on 11% SDS-PAGE and blotted to nitrocellulose membrane. FIG. 5A shows the autophosphorylation of DRP-1 and MLC phosphorylation, respectively, as seen after exposure of X-ray film. FIG. 5B shows the DRP-1 proteins by incubation of the same blot with anti-FLAG antibodies and ECL detection.

The addition of Ca2+/calmodulin to the reaction mixture increased the amount of phosphorylated MLC, in accordance with the assumption that, like DAP-kinase, DRP-1 is negatively regulated by the autoinhibitory calmodulin binding domain, and that this inhibition is removed by the binding of Ca2+ calmodulin. A catalytically inactive mutant of DRP-1, DRP-1 K42A, did not phosphorylate MLC and failed to undergo autophosphorylation even though higher amounts of DRP-1 protein were present, as can be seen from FIG. 5A. Thus, DRP-1 was found to function in vitro as a kinase that is capable of phosphorylating itself and an external substrate. This latter property is stimulated by the addition of Ca2+ and calmodulin.

DRP-1 Induces Apoptosis in a Variety of Cell Lines

The high homology to DAP-kinase in the kinase and calmodulin-binding regions suggested the value of checking whether DRP-1 is involved in apoptosis. The wild type DRP-1 and the catalytically inactive mutant of DRP-1, DRP-1 K42A, which are cloned in pCDNA3 vector, were transfected into 293 cells. To quantitate the number of apoptotic cells, these constructs were transfected with a vector expressing the GFP protein. The GFP protein was used as a marker to visualize the transfected cells and to assess the apoptotic frequency among the transfectants according to morphological alterations. Apoptotic cells were scored after 24 hours. Overexpression of the DRP-1 resulted in massive apoptotic cell death (50–60%), as compared to the basal level of apoptotic cells caused by transfection of the non-relevant gene luciferase, shown in FIGS. 6A–6B and 7.

Most of the GFP positive green cells rounded up and shrunk; some of them showed cytoplasmic blebs, and some were further fragmented into "apoptotic bodies." In addition, some of the transfected cells detached from the plate. This apoptotic cell death was only slightly lower than that of an activated DAP-kinase mutant lacking the autoinhibitory calmodulin regulatory region (ΔCaM; apoptotic values of 70–80%). In contrast, when the cells were transfected with the kinase inactive mutant of DRP-1, DRP-1 K42A, as shown in FIGS. 6A–6D and 7, no apoptosis was observed. This experiment was repeated six times with reproducible results.

Figure 8A:
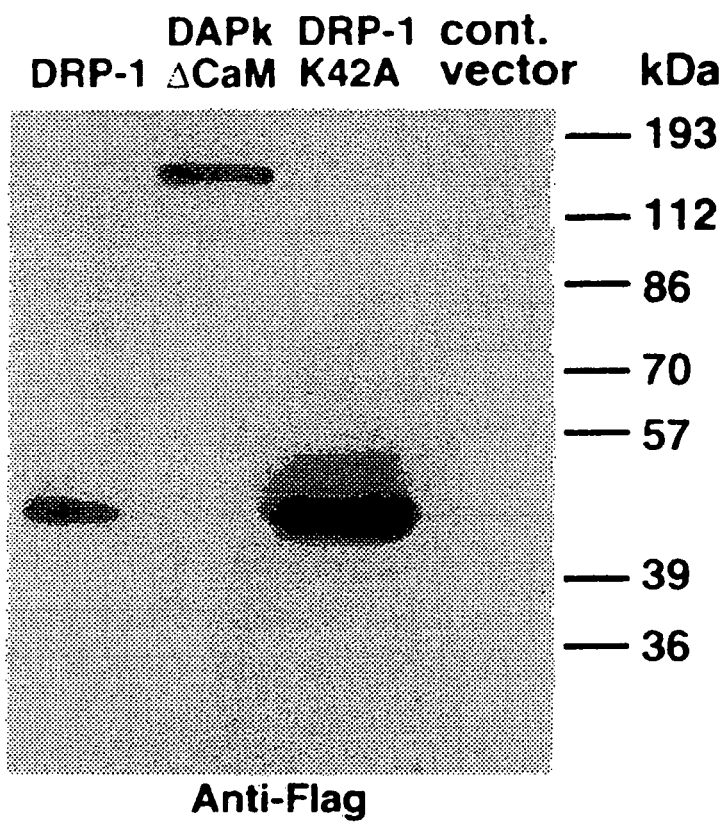
FIGS. 8A and 8B show DRP-1 protein expression in 293 transfected cells in immunoblots to anti-FLAG antibodies (FIG. 8A) and anti-vinculin antibodies (FIG. 8B).
Figure 8B:
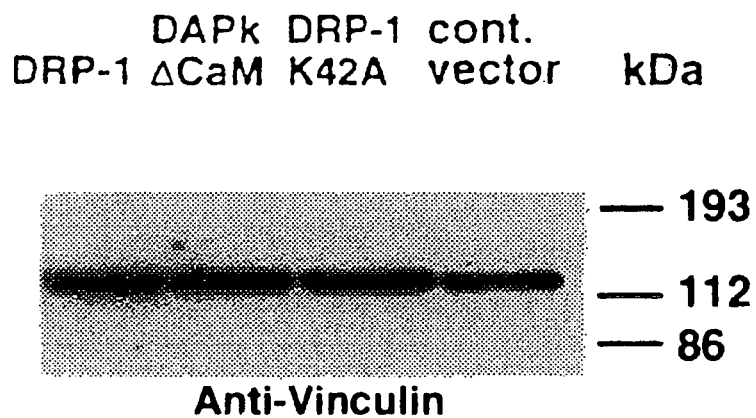

Western blot analysis of transfected cells, using anti-FLAG antibodies, confirmed the expression of both the exogenous wild type and K42A mutant of DRP-1 (FIGS. 8A and 8B). Similar results were also observed in human SV-80 fibroblasts. In another type of assay, the effect of ectopically expressed DRP-1 on the DNA content of rat embryo primary fibroblasts (REF cells) was assessed, as previously described (Kissil et al., 1999). The REFS were co-transfected with DRP-1 and a membrane-bound form of GFP and then after 48 hours subjected to FACS analysis of their DNA content. A fraction of cells displaying a sub-G1 population, indicative of cells containing fragmented DNA, appeared exclusively in the DRP-1 transfected cells but not in cells transfected with a control vector or with the DRP-1 K42A mutant form. No effect was found on cell cycle distribution of the viable cells.

Figures 6A, 6B, 6C, 6D:
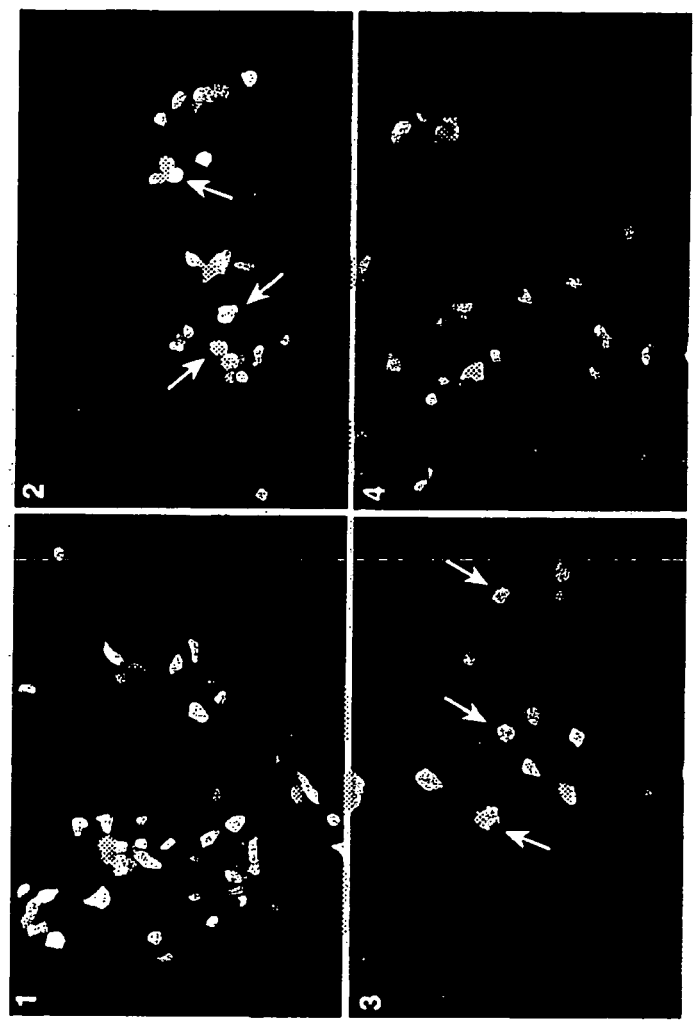
FIGS. 6A–6B show fluorescent microscope images of 293 cells transfected by pcDNA3-luciferase as a negative control (FIG. 6A), by pcDNA3-ΔCaM DAP-Kinase as positive control (FIG. 6B), by pCDNA-DRP-1 (FIG. 6C), and by pCDNA3-K42A DRP-1 (FIG. 6D). Apoptotic cells are indicated by arrows.

To obtain the results shown in FIGS. 6A–6D, $1\times10^5$ 293 cells/well were co-transfected with FLAG-tagged wild type DRP-1 or K42A mutant of DRP-1, 1.5 microgram/well and GFP, 0.5 microgram/well. GFP positive cells were visualized under fluorescent microscope and scored for the appearance of apoptotic morphology 24 hours after transfection. Apoptotic cells are indicated by arrows. The fluorescent microscopic images correspond to 293 cells transfected by pCDNA3-luciferase as negative control (FIG. 6A), pCDNA#-deltaCaM DAP-kinase as positive control (FIG. 6B), pCDNA3-DRP-1 (FIG. 6C), pCDNA3-K42A DRP-1 (FIG. 6D).

Figure 7:
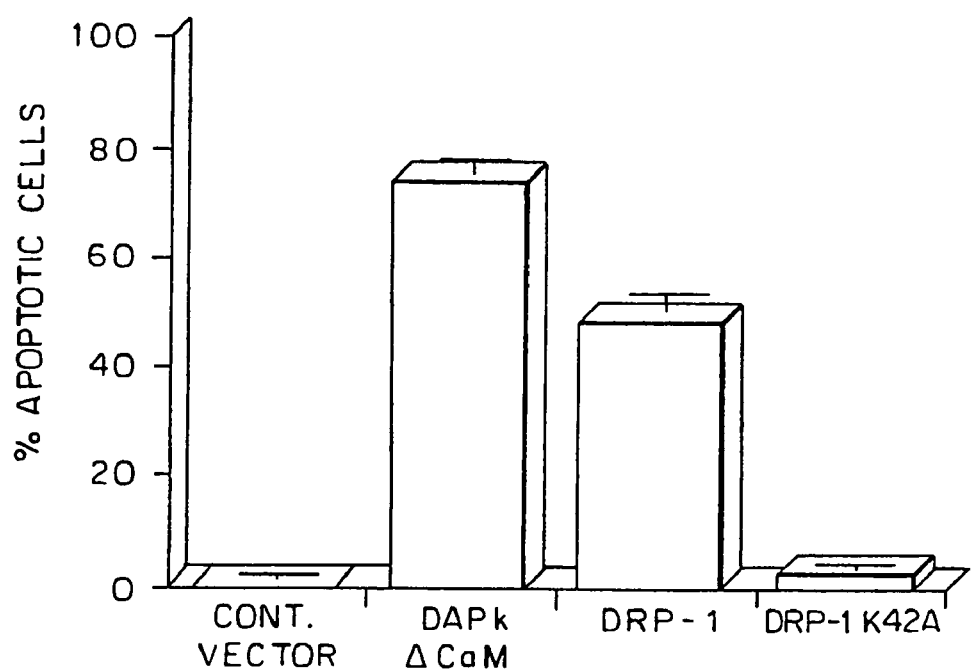
FIG. 7 shows the scores of apoptotic cells in a graph of the percentage of apoptotic cells resulting from the transfections of FIGS. 6A–6D.

In FIG. 7, graphs show the percentage of apoptotic cells resulting from the above-mentioned transfections (average±S.D. calculated from triplicates of 100 cells each). The scores were taken from the same experiment shown in FIGS. 6A–6D.

In FIGS. 8A and 8B, proteins extracted from the transfected cells were separated on 10% SDS-PAGE and blotted to nitrocellulose membrane. The blot was hybridized with anti-FLAG antibodies for DRP-1 detection and anti-vinculin antibodies to quantitate the loaded protein amounts. The proteins were prepared from the same experiments shown in FIGS. 6A–6D.

DAP Kinase Death Domain Protects From DRP-1 Induced Apoptosis

The structural homology of DRP-1 to DAP-kinase, the common regulation by Ca2+/calmodulin, and the finding that both proteins caused apoptosis upon overexpression, suggested that they function along a common apoptotic pathway. In order to test this possibility, the effect of the dominant-negative DAP-kinase death domain (DAPk DD) on DRP-1-induced cell death was analyzed. The laboratory of the present inventor showed recently that overexpression of the fragment encompassing the death domain of DAP-kinase acts as a specific dominant-negative mutant, negating the effects of the full length protein (Datta et al., 1997). As a consequence, it protected cells from TNF-alpha, Fas and FADD/MORTI-induced cell death (Datta et al., 1997).

Figure 9A:
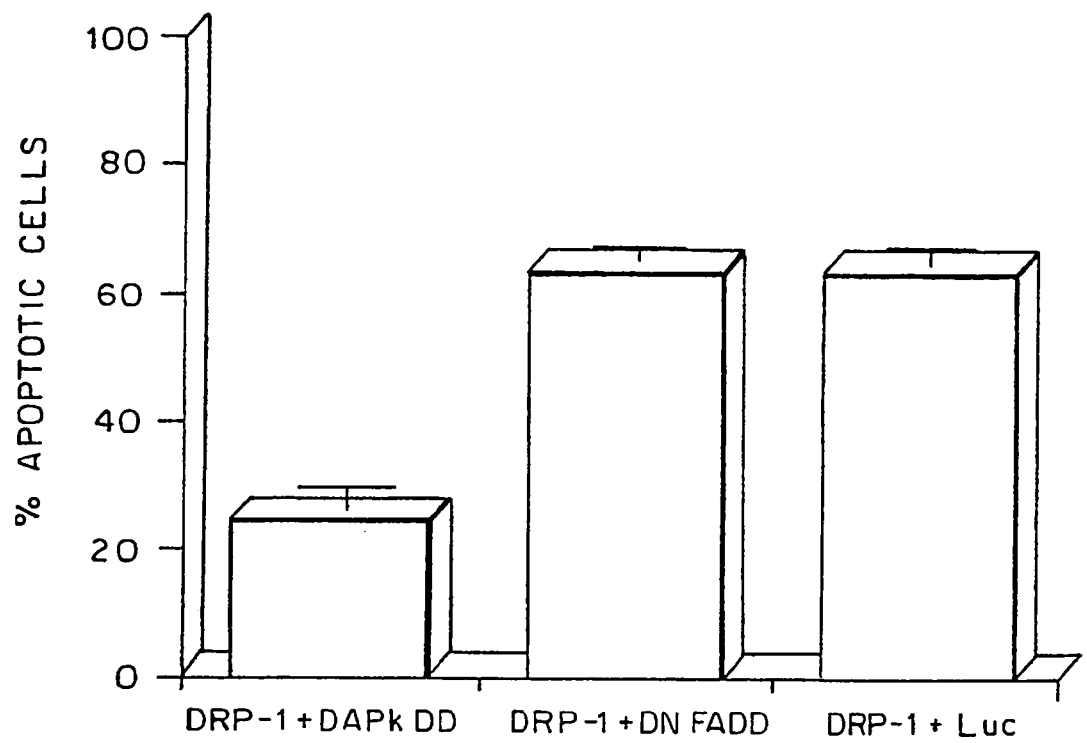
FIG. 9A shows that DAP kinase death domain protects from DRP-1 induced apoptosis.
Figure 9B:
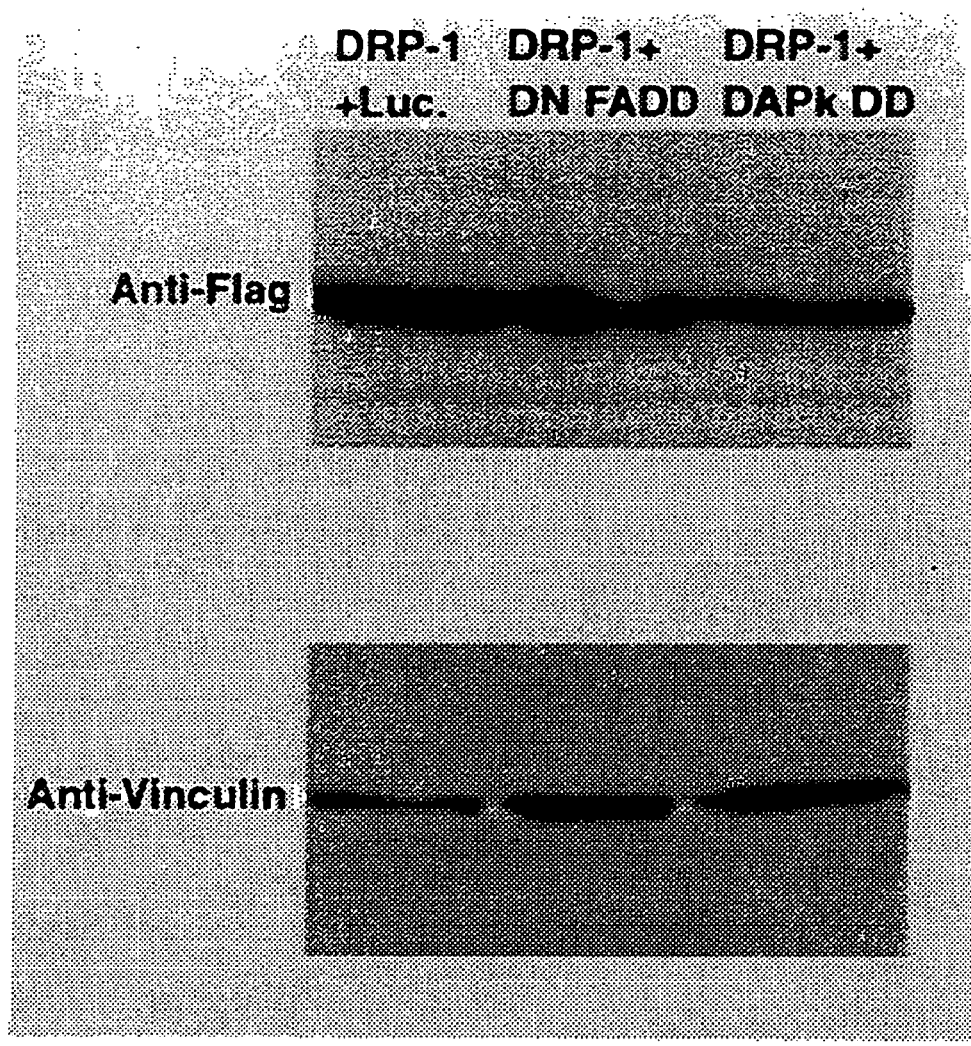
FIG. 9B shows an immunoblot of DRP-1 protein expression in 293 transfected cells.

It has now been discovered that DAPk DD protected cell death induced by DRP-1 in 293 cells. As shown in FIG. 9A, the apoptotic ratio dropped from 64.3% to 24.7%. A control transfection including DRP-1 and a non-relevant luciferase DNA excluded the possibility that this blockage was simply due to larger amount of DNA used in the transfection. Moreover, the effect of DAPk DD was specific, since the death domain of FADD failed to manifest a similar effect. (FIG. 9A). Western blot analysis of transfected cells using anti-FLAG antibodies confirmed the expression of the exogenous DRP-1 in all transfections, as shown in FIG. 9B. This experiment was repeated three times with reproducible results. The ability of the death domain of DAP-kinase to block death induced by DRP-1 implies that DAP-kinase and DRP-1 function along a common pathway.

To obtain the results shown in FIG. 9A, $1\times10^5$ cells/well of 293 cells were co-transfected with 1.2 microgram/well of FLAG-tagged wildtype DRP-1 and 0.5 microgram/well of GFP. The scores are the percentage of apoptotic cells given as average ±S.D. and calculated from triplicates of 100 cells each.

To demonstrate the DRP-1 protein expression in 293 transfected cells shown in FIG. 9B, proteins extracted from the transfected cells were separated on 10% SDS-PAGE and blotted to nitrocellulose membrane. The blot was hybridized with anti-FLAG antibodies for DRP-1 detection and anti-vinculin antibodies to quantitate the loaded protein amounts. The proteins were prepared from the same experiment shown in FIG. 9A.

Figure 10A:
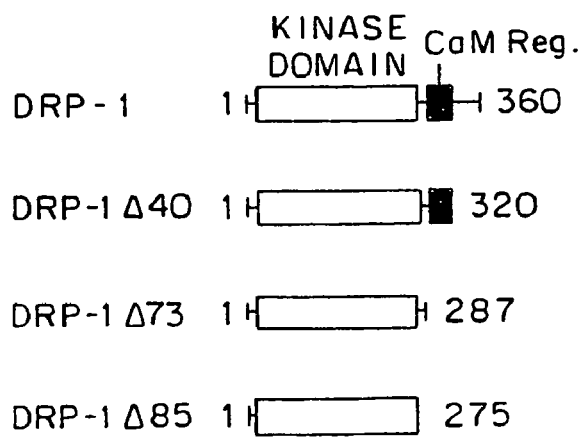
FIG. 10A shows a schematic representation of a series of generated deletion mutant.
Figure 10B:
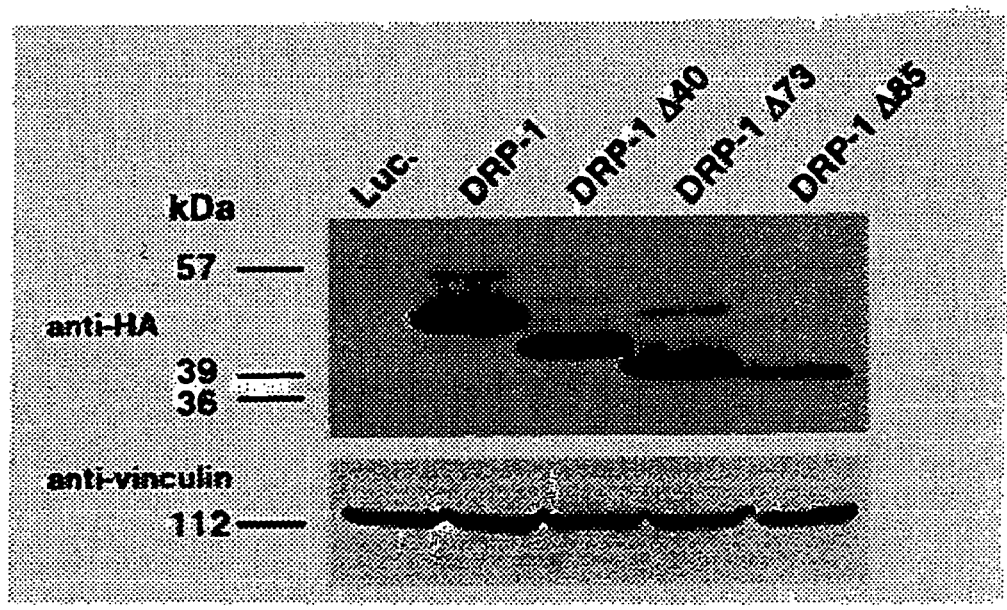
FIG. 10B shows an immunoblot containing extracts of 293 cells transiently transfected with GFP and the series of deletion mutants, (DRP-1 fragments, cloned in pCDNA3, and tagged with HA epitope at the C-terminus), as in FIGS. 8A and 8B are probed with anti-HA antibodies for DRP-1 detection and anti-vinculin antibodies to quantitate the loaded protein amounts.
Figure 11A:
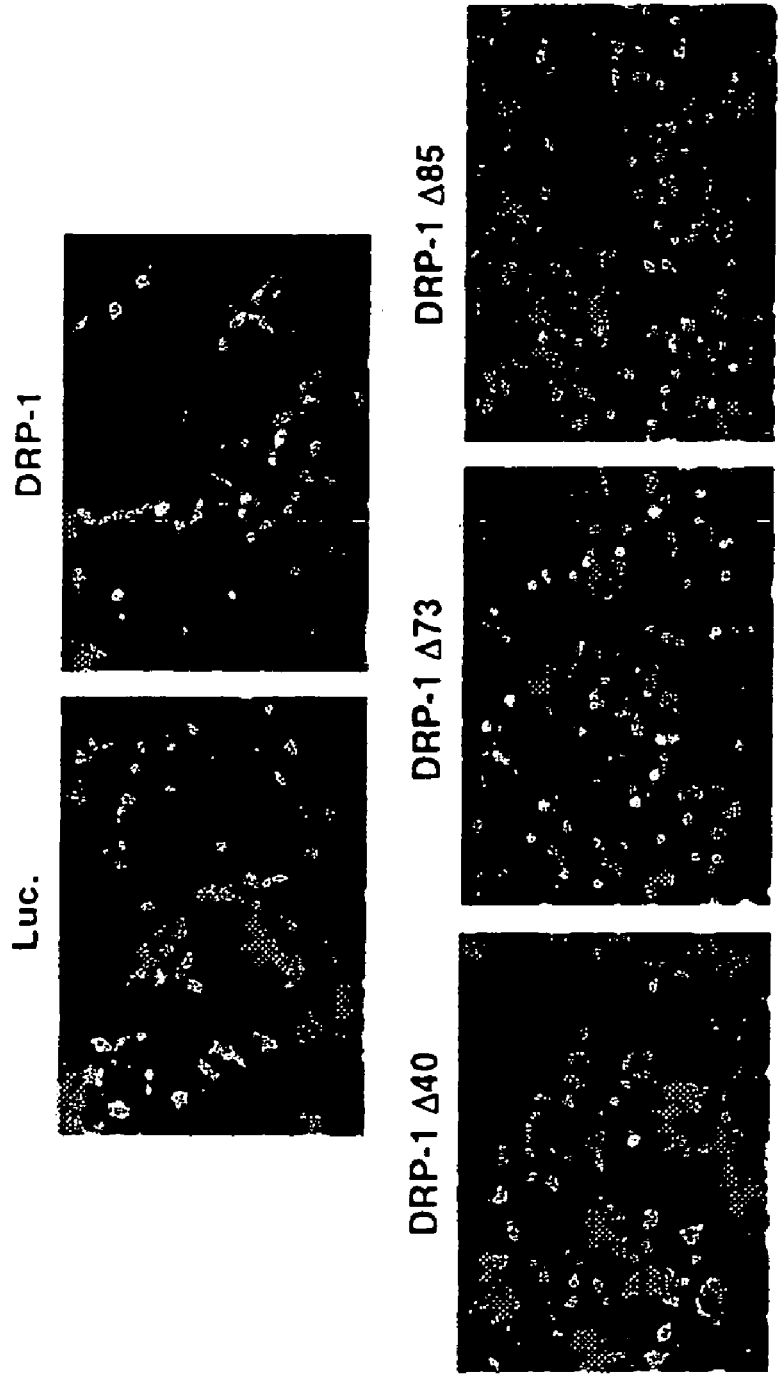
FIG. 11A shows fluorescent microscope images of the transiently transfected cells of FIG. 10B.
Figure 11B:
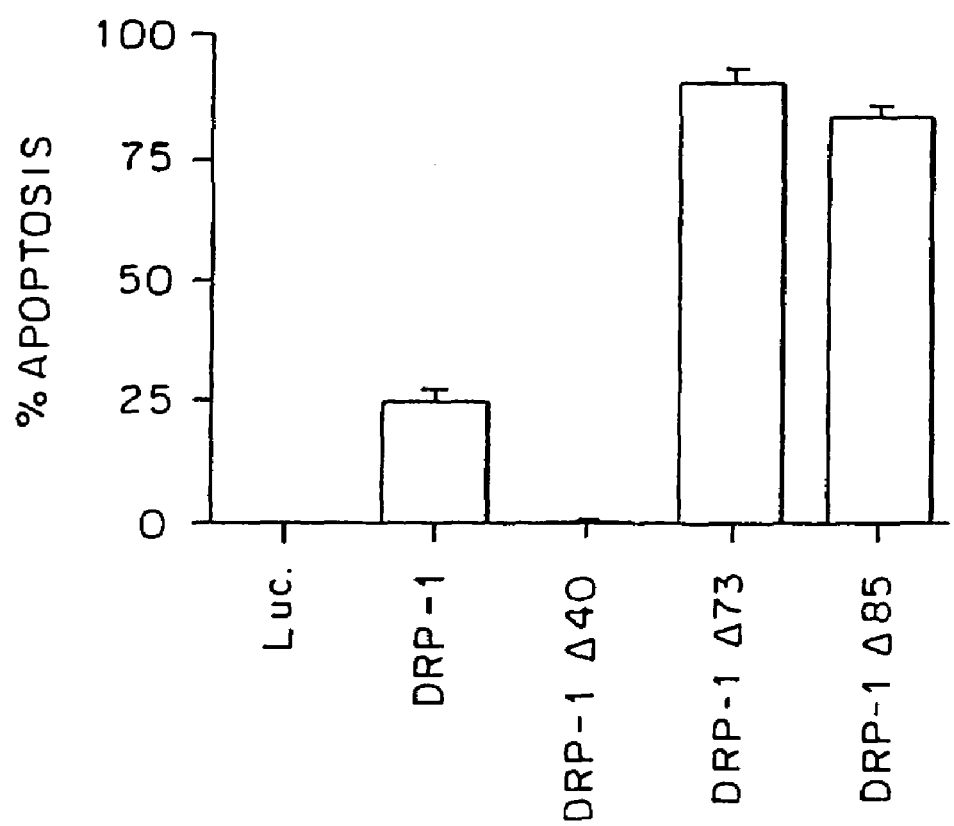
FIG. 11B shows a graph of the score in percent apoptotic cells in FIG. 11A resulting from co-transfections of 293 cells with 1–2 μg HA-tagged wild type DRP-1 or various deletion mutants of DRP-1 after 24 hours (average S.D. calculated from triplicates of 100 cells each).

Deletion of the C-Terminal Tail of DRP-1 Abolishes its Apoptotic Activity, While Further Truncation of the CaM-Regulatory Region Strongly Enhances the Apoptotic Effect In order to further understand the mode of DRP-1 action in apoptosis, constructs containing C-terminal truncations of DRP-1 tagged by HA were constructed (FIG. 10A). DRP-1 Δ40 lacks the most C-terminal part of DRP-1 which displays no homology to any known protein. DRP-1 Δ73 lacks, in addition to that, the CaM-regulatory region of DRP-1, and DRP-1 Δ85 contains only the catalytic domain. The wild type DRP-1 and the various truncation mutants of DRP-1 were transfected into 293 cells. Induction of apoptotic cell death was assayed as mentioned above in DRP-1 induced apoptosis. Overexpression of the wild type DRP-1 resulted in apoptosis (25%) while the DRP-1 Δ40 had no effect in these assays. On the other hand, further truncations of the CaM-regulatory region, yielded mutants (Δ73, Δ85) which acted as "super-killers" (~90% apoptosis) (FIGS. 11A and 11B). This experiment was repeated three times with reproducible results. Western blot analysis of transfected cells, using anti-HA antibodies confirmed the expression of all DRP-1 forms (FIG. 10B). Thus, the dependence of the apoptotic effect of DRP-1 on its kinase activity was confirmed again, since removal of the CaM-regulatory region which acts as an autoinibitory domain generates a constitutively active kinase. In addition, the existence of a positive module in the C-terminal region of DRP-1, which is necessary for its pro-apoptotic effect, provided that the CaM-regulatory effect is still present, is shown.

The C-Terminal Part of DRP-1 Functions as a Homo-Dimerization Domain

Figure 12A:
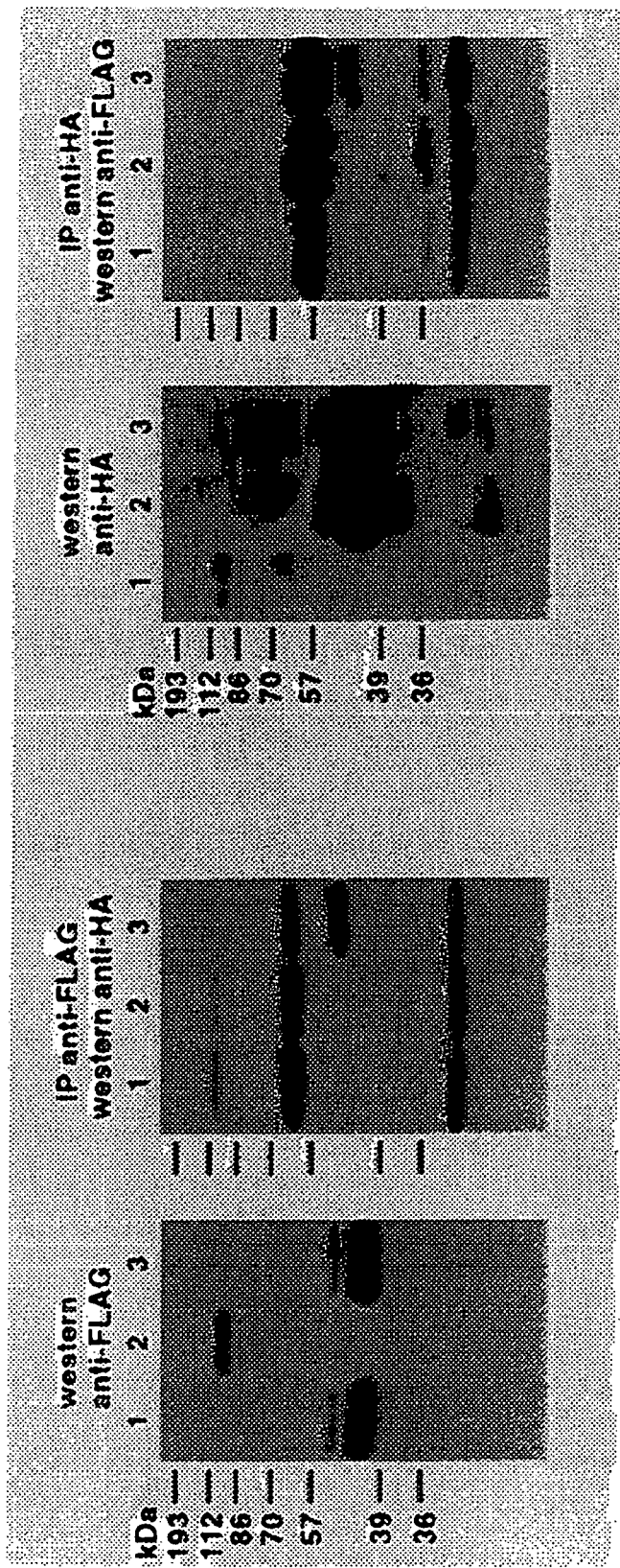

Western analysis performed on proteins extracted from 293 cells transfected by FLAG-tagged DRP-1 revealed an additional band (not shown). This observation led the present inventor to test whether DRP-1 can undergo homo-dimerization. To this aim, two constructs expressing DRP-1 fused to either FLAG or HA tags were co-transfected into 293 cells and classical pull-down experiments with each one of the two epitopes were performed. FLAG-tagged DRP-1 could be shown to bind specifically to HA-tagged DRP-1 in both IP directions (FIG. 12A, see lane 3 in both IP Panels). No binding of DRP-1-HA to FLAG beads or to the irrelevant cytoplasmic protein RFX-ΔSmaI could be observed (FIG. 12A, see IP anti-FLAG panel, lanes 2 or 1+2, respectively). Also non-specific binding of DRP-1-FLAG to HA bead or to RFX-ΔSmaI protein could not be detected (FIG. 12A, see IP anti-HA panel, lanes 1 or 1+2, respectively). Western analyses confirmed the expression of all proteins in these cell extracts (FIG. 12A, see Western panels).

The observation that a C-terminal truncation of 40 amino acids in DRP-1 abolished its apoptotic effect upon ectopic expression in 293 cells, prompted the present inventor to test whether this domain may be involved in the homo-dimerization of DRP-1. DRP-1-FLAG was co-expressed in conjugation with the various deletion mutants of DRP-1 tagged by HA. A strong binding of DRP-1-FLAG to the wild type DRP-1-HA was detected, whereas the binding to DRP-1 Δ40 was mostly abolished (FIG. 12B, upper IP panel, compare lane 1 to 2–4). Western analysis confirmed the expression of wild type DRP-1-HA and all other DRP-1-HA deletion mutants in these transfections (FIG. 12B, see Western panel). Lower IP panel confirmed the expression of wild type DRP-1-FLAG in all these transfections. Thus, the present inventor concluded that a region spanning the C-terminal 40 amino acids of DRP-1 is responsible for its homo-dimerization. This homo-dimerization is probably required for the apoptotic effect of DRP-1, since DRP-1-Δ40 has lost the ability to induce apoptosis in 293 cells (FIGS. 11A and 11B).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Anderson, P., "Kinase cascades regulating entry into apoptosis," *Microbiol. Mo. Biol. Rev.,* 61, 33–46, 1997.

Ausubel et al., *Current Protocols in Molecular Biology*, Green Publications and Wiley Interscience, New York, 1987–1999.

Basu, S., and Kolesnick, R, "Stress signals for apoptosis: ceramide and c-Jun kinase," *Oncogene,* 17, 3277–3285, 1998.

Bokoch, G. M., "Caspase-mediated activation of PAK2 during apoptosis: proteolytic kinase activation as a general mechanism of apoptotic signal transduction?", *Cell death diff.,* 5, 637–645, 1998.

Cardone, M. H., Salveson, G. S., Widmann, C., Johnson, G. And Frisch, S. M., "The regulation of anoikisis: MEKK-1 activation requires cleavage by caspasses.", *Cell,* 90, 315–323, 1997.

Cardone, M. H., Roy, N., Stennicke, H. R., Salvesen, G. S., Franke, T. F., Stanbridge, E., Frisch, S., and Reed, J. S., "Regulation of cell death protease caspasse-9 by phosphorylation.", *Science,* 282, 318–321, 1998.

Cohen, O., Feinstein, E., and Kimchi, A., "DAP-kinase is a Ca2+/calmodulin-dependent, cytoskeletal-associated protein kinase, with cell death-inducing functions that depend on its catalyitic activity.", *EMBO. J.,* 16, 998–1008, 1997.

Cohen, O., Inbal, B., Kissil, J. L., Feinstein, E., Spivak, T., and Kimchi; A., "DAP-kinase participates in TNF-α and Fas-induced apoptosis and its function requires the death domain.", *J. Cell. Biol.*, in press, 1999.

Datta, S. R., Dudek, H., Tao, X., Masters, S., Fu, H., Gotoh, Y., and Greenberg, M. E., "Akt phosphorylation of BAD couples survival signals to the cell-intrinsic death machinery.," *Cell*, 91, 231–241, 1997.

Deiss, L. P., Feinstein, E., Berissi, H., Cohen, O., and Kimchi, A., "Identification of a novel serine/threonine kinase and a novel 15-kD protein as potential mediators of the gamma interferon-induced cell death.", *Genes Dev.*, 9, 15–30, 1995.

Deiss, L. P. and Kimchi, A., "A genetic tool used to identify thioredoxin as a mediator of a growth inhibitory signal.", *Science*, 252, 117–120, 1991.

del Peso, L., Gonzalez-Garcia, M., Page, C., Herrera, R, and Nunez, G., "Interleukin-3-induced phosphorylation of BAD through the protein kinase Akt.", *Science*, 282, 318–321, 1997.

Eshhar, Z. et al., *Br. J. Cancer Suppl.*, 10, 27–9, 1990.

Feinstein, E., Kimchi, A., Wallach, D., Boldin, M., and Varfolomeev, E., "The death domain: a module shared by proteins with diverse cellular functions.", *Trends Biochem. Sci.*, 20, 342–344, 1995.

Green, D., and Kroemer, G., "The central executioners of apoptosis: caspases or mitochondria?" *Trends Cell Biol.*, 8, 267–271, 1998.

Gross, G. et al., *Proc, Natl. Acad. Sci. USA*, 86, 10024–8, 1989.

Hanks, S. K., and Quinn, A. M., "Protein kinase catalytic domain sequence database: identification of conserved features of primary structure and classification of family members.", *Methods Enzymol.*, 200, 38–62, 1991.

Inbal, B., Cohen, O., Polak-Charcon, S., Kopolovic, J., Vadai, E., Eisenbach, L., and Kimchi, A., "DAP kinase links the control of apoptosis to metastasis.", *Nature*, 390, 180–184, 1997.

Inbal, B., Kissil, J. K., Cohen, O., Spivak-Kroizman, T., and Kimchi, A., "The DAP-related protein kinases-a novel subfamily of serine/threonine kinases with a possible link to apoptosis.", submitted, 1999.

Jacobson, M. D., Weil, M., and Raff M. C., "Programmed cell death in a animal development." *Cell*, 88, 347–354, 1997.

Kawai, T., Matsumoto, M., Takeda, K., Sanjo, H., and Akira, S., "ZIP kinase, a novel serine/threonine kinase which mediates apoptosis.", *Mol. Cell Biol.*, 18, 1642–1651, 1998.

Kelliher, M. A., Grimm, S., Ishida, Y., Kuo, F., Stanger, B. Z., and Leder, P., "The death domain kinase RIP mediates the TNF-induced NF-kappaB signal.", *Immunity*, 8, 297–303, 1998.

Kimchi, A., *J. Cell. Biochem.*, 50, 1–9, 1992.

Kimchi, A., "DAP genes: novel apoptotic genes isolated by a functional approach to gene cloning.", *Biochim. Biophys. Acta* 1377, F13–33, 1998.

Kissil, J. L., and Kimchi, A., "Death-associated proteins: from gene identification to a the analysis of their apoptotic and tumur suppressive functions.", *Mol. Med. Today*, 4, 268–74, 1998.

Kissil J. L., Cohen, O., Raveh, T., and Kimchi, A., "DAP-kinase loss of expression in various carcinoma and B-cell lymphoma cell lines: possible implications for role as tumor suppressor gene.", *EMBO J.*, 18, 353–362, 1999.

Kogel, D., Plottner, O., Landsberg, G., Christian, S., and Scheidtmann, K. H., "Cloning and characterization of Dlk a novel serine/threonine kinase that is tightly associated with chromatin and phophorylates core histones.", *Oncogene*. 17, 2645–2654, 1998.

Levy et al., *Mol. Cell. Biol.*, 13, 7942–7952, 1993.

Levy-Strumpf, N., and Kimchi, A., "Death associated proteins (DAPs): from gene identification to the analysis of their apoptotic and tumor suppressive functions." *Oncogene*, 17, 3331–3340, 1998.

Maundrell, K., Antonsson, B., Magnenat, E., Camps, M., Muda, M., Chabert, C., Gillieron, C., Boschert, U., Vial-Knecht, E., Martinou, J. C., and Artkinstall, S., "Bcl-2 undergoes phosphorylation by c-Jun N-terminal kinase/stress-activated protein kinases in the presence of the constitutively active GTP-binding protein Racl.", *J. Biol. Chem.*, 272, 25238–25342, 1997.

McCarthy, J. V., Ni., J., and Dixit, V. M., "RIP2 is a novel NF-kappaB-activating and cell death-inducing kinase, *J. Biol. Chem.*, 273, 16968–75, 1998.

Meinkoth et al., *Anal. Biochem.*, 138, 267–284, 1984.

Park, J., Kim., I., Oh, Y. J., Lee, K., Han, P. L., and Choi, E. J., "Activation of c-Jun N-terminal kinase antagonizes an anti-apoptotic action of Bcl-2.", *J. Biol. Chem.*, 272, 16725–16728, 1997.

Peitenpol et al, *Cell*, 61, 777–785, 1990.

Sambrooke et al., *Molecular Cloning: A Laboratory Manual*, 2$^{nd}$ Ed., Cold Spring Harbor Press, Cold Spring Harbor, N.Y., 1989.

Sanjo, H., Kawai, T., and Akira, S., "DRAKS, novel serine/threonine kinases related to death-associated protein kinase that trigger apoptosis.", *J. Biol. Chem.*, 273, 29066–29071, 1998.

Stanger, B. Z., Leder, P., Lee, T. H., Kim, E., and Seed, B., "RIP: a novel protein containing a death domain that interacts with Fas/APO-1 (CD95) in yeast and causes cell death.", *Cell*, 81, 513–523, 1995.

Sun, X., Lee, J., Navas, T., Baldwin, D. T., Stewart, T. A., and Dixit, V. M., "RIP3, a Novel Apoptosis-inducing Kinase.", *J. Biol. Chem.*, 274, 16871–16875, 1999.

Thompson, J. D., Higgins, D. G., Gibson, T., J., "CLUSTAL W: improving the sensitivity of progressive multiple sequence alignment through sequence weighting, position-specific gap penalties and weight matrix choice.", *Nucleic Acids Res.*, 22, 4673–4680, 1994.

Verheij, M., Ruiter, G. A., Zerp, S. F., Van Blitterswijk, W. J., Fuks, Z. Haimovitz-Friedman, A., and Bartelink, H., "The role of the stress-activated protein kinase (SAPK/JNK) signaling pathway in radiation-induced apoptosis.", *Radiother. Oncol.*, 47, 225–232, 1998.

Wahl et al., *J. Nucl. Med.*, 24, 316–325, 1983.

White, E., "Life, death and the pursuit of apoptosis.", *Genes Dev*, 10, 1–15, 1996.

Yang, X., Khosravi-Far, R., Chang, H. Y., and Baltimore, D., *Cell*, 89, 1067–1076, 1997.

Yu, P. W., Huang, B. C., Shen, M., Quast, J., Chan, E., Xu, X, Nolan, G. P., Payan, D. G. and Luo, Y., "Identification of RIP3, a RIP-like kinase that activates apoptosis and Nfkappa B.", *Curr. Biol.*, 9, 539–42, 1999.

What is claimed is:

1. An isolated polypeptide, which is a calmodulin-dependent serine/threonine kinase, or a fragment thereof, selected from the group consisting of:
   (A) a polypeptide which is capable of inducing cell death (apoptosis) and comprises the amino acid sequence of SEQ ID NO:2;
   (B) a polypeptide which has a property of being capable of inducing cell death and has at least 90% sequence identity to the amino acid sequence of SEQ ID NO:2;
   (C) a fragment of a polypeptide of (A) which is capable of inducing cell death; and
   (D) a fragment of a polypeptide of (A) which lacks the property of being capable of inducing cell death and which inhibits the ability of the polypeptide (A) to induce cell death.

2. An isolated DNA molecule comprising a nucleotide sequence encoding the polypeptide or fragment thereof according to claim 1.

3. The isolated DNA molecule according to claim 1, wherein said nucleotide sequence encodes the amino acid sequence of SEQ ID NO:2.

4. The isolated DNA molecule according to claim 3, wherein said nucleotide sequence corresponds to nucleotides 62 to 1141 of SEQ ID NO:1.

5. The isolated DNA molecule according to claim 3, which consists of the nucleotide sequence corresponding to nucleotides 62 to 1141 of SEQ ID NO:1.

6. An isolated DNA molecule which hybridizes to the DNA molecule of claim 5 under highly stringent conditions and encodes a calmodulin-dependent serine/threonine kinase having the property of being capable of inducing cell death.

7. A polypeptide capable of inducing cell death, consisting of an amino acid sequence selected from the group consisting of amino acid residues 13 to 275 of SEQ ID NO:2 and an amino acid sequence having at least 90% sequence identity to residues 13 to 275 of SEQ ID NO:2.

8. An isolated DNA molecule comprising a nucleotide sequence encoding the polypeptide of claim 7.

9. The isolated DNA molecule according to claim 8, wherein said nucleotide sequence encodes the amino acid sequence corresponding to residues 13 to 275 of SEQ ID NO:2.

10. The isolated DNA molecule according to claim 9, wherein said nucleotide sequence hybridizes to nucleotides 98 to 886 of SEQ ID NO:1 under highly stringent conditions and encodes a polypeptide capable of inducing cell death.

11. A polypeptide capable of inhibiting the ability of the polypeptide of SEQ ID NO:2 to induce cell death, consisting of an amino acid sequence selected from the group consisting of amino acid residues 321 to 360 of SEQ ID NO:2 and an amino acid sequence having at least 85% sequence identity to residues 321 to 360 of SEQ ID NO:2.

12. An isolated DNA molecule consisting of a nucleotide sequence encoding the polypeptide of claim 11.

13. The isolated DNA molecule according to claim 12, wherein said nucleotide sequence encodes the amino acid sequence corresponding to residues 321 to 360 of SEQ ID NO:2.

14. The isolated DNA molecule according to claim 13, wherein said nucleotide sequence hybridizes to nucleotides 1022 to 1141 of SEQ ID NO:1 under highly stringent conditions and encodes a polypeptide capable of inducing cell death.

15. A vector comprising the isolated DNA molecule according to claim 2.

16. A host cell transformed with the isolated DNA molecule according to claim 2.

17. A composition comprising a polypeptide according to claim 1 and a pharmaceutically acceptable excipient, carrier, diluent or auxiliary agent.

18. A single stranded RNA molecule having 17 to 30 nucleotides in length that is complementary to at least a portion of the isolated messenger RNA molecule which is the transcription product of the DNA sequence encoding a polypeptide of SEQ ID NO:2, wherein said complementary single stranded RNA molecule is capable of hybridizing to said isolated messenger RNA to prevent its translation into said polypeptide of SEQ ID NO:2.

19. A method of neutralizing a messenger RNA molecule, which is the transcription product of the DNA sequence encoding a polypeptide of SEQ ID NO:2, comprising the step of contacting the single stranded RNA molecule of claim 18 with the messenger RNA to neutralize the messenger RNA by hybridizing thereto and preventing its translation into the polypeptide of SEQ ID NO:2.

20. A composition comprising a polypeptide according to claim 8, and a pharmaceutically acceptable excipient, carrier, diluent or auxiliary agent.

21. A composition comprising a polypeptide according to claim 11, and a pharmaceutically acceptable excipient, carrier, diluent or auxiliary agent.

22. The polypeptide of claim 1, wherein said polypeptide (B) has at least 95% sequence identity to the amino acid sequence of SEQ ID NO:2.

23. The polypeptide of claim 7 which has at least 90% sequence identity to residues 13 to 275 of SEQ ID NO:2.

24. The polypeptide of claim 11 which has at least 95% sequence identity to residues 13 to 275 of SEQ ID NO:2.

25. The polypeptide of claim 11 which has at least 90% sequence identity to residues 321 to 360 of SEQ ID NO:2.

26. The polypeptide of claim 11 which has at least 95% sequence identity to residues 321 to 360 of SEQ ID NO:2.

27. A vector comprising the isolated DNA molecule according to claim 12.

28. A host cell-transformed with the isolated DNA molecule according to claim 12.

29. A single stranded RNA molecule having 100% complementarity to at least a portion of the isolated messenger RNA molecule which is the transcription product of the DNA sequence encoding a polypeptide of SEQ ID NO:2, wherein the complementary single stranded RNA molecule is capable of hybridizing to said isolated messenger RNA molecule to prevent its translation into said polypeptide of SEQ ID NO:2.

30. A method of neutralizing a messenger RNA molecule, which is the transcription product of the DNA sequence encoding a polypeptide of SEQ ID NO:2, comprising the step of contacting the single stranded RNA molecule of claim 29 with the messenger RNA to neutralize the messenger RNA by hybridizing thereto and preventing its translation into the polypeptide of SEQ ID NO:2.

* * * * *